US008354385B2

(12) United States Patent
Boj et al.

(10) Patent No.: US 8,354,385 B2
(45) Date of Patent: Jan. 15, 2013

(54) MODULATION OF TRPV EXPRESSION LEVELS

(75) Inventors: Maria Del Carmen Acosta Boj, Alicante (ES); Juana Gallar Martinez, Alicante (ES); Angela Sesto Yague, Madrid (ES); Carlos Belmonte Martinez, Alicante (ES); Ana Isabel Jimenez Anton, Madrid (ES); Maria Concepcion Jimenez Gomez, Madrid (ES)

(73) Assignee: Sylentis S.A.U., Madrid (ES)

( * ) Notice: Subject to any disclaimer, the term of this patent is extended or adjusted under 35 U.S.C. 154(b) by 416 days.

(21) Appl. No.: 12/090,426

(22) PCT Filed: Oct. 20, 2006

(86) PCT No.: PCT/GB2006/050342
§ 371 (c)(1),
(2), (4) Date: Jun. 25, 2010

(87) PCT Pub. No.: WO2007/045930
PCT Pub. Date: Apr. 26, 2007

(65) Prior Publication Data
US 2010/0286230 A1    Nov. 11, 2010

(30) Foreign Application Priority Data
Oct. 20, 2005   (GB) .................................. 0521351.7

(51) Int. Cl.
*A61K 48/00*    (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| 4,343,794 A | 8/1982 | Podos et al. |
| 4,617,299 A | 10/1986 | Knepper |
| 4,652,586 A | 3/1987 | Nathanson |
| 4,757,089 A | 7/1988 | Epstein |
| 4,812,448 A | 3/1989 | Knepper |
| 5,075,323 A | 12/1991 | Fain et al. |
| 5,242,943 A | 9/1993 | Louis et al. |
| 5,260,059 A | 11/1993 | Acott et al. |
| 5,464,866 A | 11/1995 | Clark et al. |
| 5,545,626 A | 8/1996 | Stein et al. |
| 5,585,401 A | 12/1996 | Brandt et al. |
| 6,365,576 B1 | 4/2002 | Carr |
| 6,372,249 B1 | 4/2002 | Smith et al. |
| 6,489,307 B1 | 12/2002 | Phillips et al. |
| 7,176,304 B2 | 2/2007 | McSwiggen et al. |
| 7,294,504 B1 | 11/2007 | Wang |
| 7,462,602 B2 | 12/2008 | Schultz et al. |
| 7,521,431 B2 | 4/2009 | Reich et al. |
| 7,579,457 B2 | 8/2009 | Khvorova et al. |
| 7,592,324 B2 | 9/2009 | Shepard et al. |
| 7,592,325 B2 | 9/2009 | Jimenez et al. |
| 7,618,814 B2 | 11/2009 | Bentwich |
| 7,655,789 B2* | 2/2010 | Khvorova et al. ........... 536/24.5 |
| 7,687,665 B2 | 3/2010 | Yao et al. |
| 7,691,997 B2 | 4/2010 | Khvorova et al. |
| 7,700,575 B2 | 4/2010 | Andrew et al. |
| 8,090,542 B2 | 1/2012 | Khvorova et al. |
| 2002/0055536 A1 | 5/2002 | DeWitte et al. |
| 2002/0114784 A1 | 8/2002 | Li et al. |
| 2002/0165158 A1 | 11/2002 | King |
| 2004/0029275 A1* | 2/2004 | Brown et al. ................. 435/375 |
| 2004/0115641 A1 | 6/2004 | Cowsert et al. |
| 2004/0167090 A1 | 8/2004 | Monahan et al. |
| 2004/0198640 A1 | 10/2004 | Leake et al. |
| 2004/0209832 A1 | 10/2004 | McSwiggen et al. |
| 2004/0224405 A1 | 11/2004 | Leake et al. |
| 2004/0235031 A1 | 11/2004 | Schultz et al. |
| 2004/0259247 A1 | 12/2004 | Tuschl et al. |
| 2004/0266707 A1 | 12/2004 | Leake et al. |
| 2005/0020521 A1 | 1/2005 | Rana |
| 2005/0165049 A1 | 7/2005 | Hulme et al. |
| 2005/0171039 A1 | 8/2005 | McSwiggen et al. |
| 2005/0208658 A1 | 9/2005 | Castonguay |
| 2005/0255487 A1 | 11/2005 | Khvorova et al. |
| 2006/0058266 A1 | 3/2006 | Manoharan et al. |
| 2006/0094032 A1 | 5/2006 | Fougerolles et al. |
| 2006/0172963 A1 | 8/2006 | Shepard et al. |
| 2006/0172965 A1 | 8/2006 | Shepard et al. |
| 2006/0257851 A1 | 11/2006 | Bentwich |
| 2007/0049543 A1 | 3/2007 | McSwiggen et al. |
| 2007/0093435 A1 | 4/2007 | Andrews et al. |
| 2007/0167384 A1 | 7/2007 | Leake et al. |
| 2009/0326044 A1 | 12/2009 | Shepard et al. |

FOREIGN PATENT DOCUMENTS

EP        1 527 176        1/2007

(Continued)

OTHER PUBLICATIONS

Schubert et al. J. Mol. Biol. May 2005, vol. 348: 883-893.*
Gavva et al. (J. of Pharmacology & Experimental Therapeutics 2005, vol. 313:474-484).*
Grunweller, et al. (2003, Nuc. Acids Res., v.31 :3185-93).*
Bass (2001, Nature, v.411:428-9).*
Elbashir, et al. (2002, Methods, v.26 :199-213).*
Fattal et al., "Antisense Oligonucleotides, Aptamers and siRNA: Promises for the Treatment of Ocular Disease," Arch. Soc. Esp. Oftalmol, 8(1), pp. 1-4, 2006.
Ghate et al., "Barriers to Glaucoma Drug Delivery," J. Glaucoma, 17(2), pp. 147-156, Mar. 2008.
Gonzalez et al., "Reduction of Capsaicin-Induced Ocular Pain and Neurogenic Inflammation by Calcium Antagonists," Investigative Ophthalmology & Visual Science, 34(12), pp. 3329-3335, Nov. 1993.

(Continued)

*Primary Examiner* — Kimberly Chong
(74) *Attorney, Agent, or Firm* — Margaret B. Brivanlou; King & Spalding

(57) ABSTRACT

The present invention relates to methods and compositions for the treatment and/or the prevention of conditions related to high levels of expression and/or activity of the transient receptor potential vanilloid-1 (TRPV1). Amongst others, the conditions to be treated are eye conditions such as discomfort and altered sensitivity of the cornea following refractive surgery, use of contact lenses, dry eyes and diabetic retinopathy.

17 Claims, 10 Drawing Sheets

FOREIGN PATENT DOCUMENTS

| | | |
|---|---|---|
| GB | 240856 | 4/2005 |
| GB | 2406568 | 4/2005 |
| WO | 03/059267 A2 | 7/2003 |
| WO | WO 03/057840 | 7/2003 |
| WO | 03070744 | 8/2003 |
| WO | WO 03/070744 | 8/2003 |
| WO | WO 03/087367 | 10/2003 |
| WO | WO 2004/009794 | 1/2004 |
| WO | WO 2004/009796 | 1/2004 |
| WO | 2004029212 | 4/2004 |
| WO | WO 2004/029212 | 4/2004 |
| WO | 2004042046 | 5/2004 |
| WO | WO 2004/042024 | 5/2004 |
| WO | WO 2005/032493 | 4/2005 |
| WO | 2005040106 | 5/2005 |
| WO | 2005044976 | 5/2005 |
| WO | 2005045037 | 5/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/083945 | 8/2006 |
| WO | WO 2006/084217 | 8/2006 |
| WO | WO 2006/099353 | 9/2006 |

OTHER PUBLICATIONS

Nie et al., "The Potential Therapeutic of siRNA Eye Drops in Ocular Diseases," Bioscience Hypotheses, 2, pp. 223-225, 2009.

Abrams et al., "Comparison of Three Tonometers for Measuring Intraocular Pressure in Rabbits," Invest Ophthalmol Vis Sci. Apr. 1996, 37(5):940-944.

Achenbach et al., Oligonucleotide-Based Knockdown Technologies: Antisense Versus RNA Interference, ChemBioChem., 4, pp. 928-935, 2003.

Akashi et al., "Suppression of Gene Expression by RNA Interference in Cultured Plant Cells," Antisense Nucleic Acid Drug Dev, 2001, 11(6):359-367.

Amaratunga et al., "Inhibition of Kinesin Synthesis and Rapid Anterograde Axonal Transport in Vivo by an Antisense Oligonucleotide," The Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191, Apr. 2000.

Ambion, "The Basics: RNase Control," printout from website <<http://web.archive.org/web/20041207234247>>, dated 2004, retrieved on Sep. 17, 2009.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.

Banan et al., "The Ins and Outs of RNAi in Mammalian Cells," Current Pharmaceutical Biotechnology, 5, pp. 441-450, 2004.

Banerjee et al., "Control of Developmental Timing by Small Temporal RNAs: a Paradigm for RNA-mediated Regulation of Gene Expression," Bioessays, 2002, 24(2):119-129.

Barar J. et al., "Ocular novel drug delivery" impacts of membranes and barriers, Expert Opin. Drug Deliv., 5(5): 567-81, 2008.

Bass, "The Short Answer," Nature, vol. 411, pp. 428-429, 2001.

Bhattacharya et al., "Cochlin Deposits in the Trabecular Meshwork of the Glaucomatous DBA/2J mouse," Exp Eye Res., May 2005 80(5):741-744.

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec. 3, 2004.

Bill, "Movement of Albumin and Dextran," Arch. Opthal., vol. 74, pp. 248-252, Aug. 1965.

Borrás, "Gene Expression in the Trabecular Meshwork and the Influence of Intraocular Pressure," Progress in Retinal and Eye Research, 22, 435-463, 2003.

Bosher et al., "RNA Interference: Genetic Wand and Genetic Watchdog." Nat Cell Biol, 2000, 2(2):E31-6.

Braasch et al., "Novel Antisense and Peptide Nucleic Acid Strategies for Controlling Gene Expression," Biochemistry, 2002, 41(14):4503-4510.

Brummelkamp et al., "A System for Stable Expression of Short Interfering RNAs in Mammalian Cells," Science, American Association for the Advancement of Science, 2002, 296(5567):550-553.

Busch et al., "Adenylyl Cyclase in Human and Bovine Trabecular Meshwork," Investigative Ophthalmology & Visual Science, 34(10), pp. 3028-3034, Sep. 1993.

Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.

Caballero et al., "Inefficient Processing of an Olfactomedin-Deficient Myocilin Mutant: Potential Physiological Relevance to Glaucoma," Biochemical and Biophysical Research Communications, 282, 662-670, 2001.

Caplen et al., "Specific inhibition of Gene Expression by Small Double Stranded RNAs in Invertebrate and Vertebrate Systems," Proc. Natl. Acad. Sci. USA, 2001,98: 9742-9747.

Cho et al., "Small Interfering RNA-Induced TLR3 Activation Inhibits Blood and Lymphatic Vessel Growth," PNAS, pp. 1-6, Dec. 5, 2008.

Comes N. and Borrás T, "Functional delivery of synthetic naked siRNA to the human trabecular meshwork in perfused organ cultures," Molec. Vision, 13: 1363-74, 2007.

Costagliola et al., "Effect of Oral Losartan Potassium Administration on Intraocular Pressure in Normotensive and Glaucomatous Human Subjects," Exp Eye Res., Aug. 2000, 71(2):167-171.

Costagliola et al., "Effect of Oral Captopril (SQ 14225) on Intraocular Pressure in Man," Eur. J. Opthalmol, Jan. 1995, 5(1):19-25.

Crooke et al., "Nucleotides in Ocular Secretions: Their Role in Ocular Physiology," Pharmacology & Therapeutics, 119, pp. 55-73, 2008.

Cullinane et al., "Renin-angiotensin System Expression and Secretory Function in Cultured human Ciliary Cody Nonpigmented Epithelium," Br J Ophthalmol. Jun. 2002, 86(6):6766-83.

Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.

Diffen, DNA vs. RNA-Difference and Comparison, retrieved from <<http://www.diffen.com/difference/Dna_vs_Rna>> on May 21, 2009.

Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.

Elabashir et al., "Duplexes of 21-Nucleotide RNAs mediate RNA interference in Cultured Mammalian Cells," Nature, May 24, 2001, 411(6836):494-498.

Elbashir et al., "Functional Anatomy of siRNAs for Mediating Efficient RNAi in Drosophila melanogaster Embryo Lysate," EMBO Journal, vol. 20, No. 23, pp. 6877-6888, 2001.

Elbashir et al., "RNA Interference is Mediated by 21- and 22-Nucleotide RNAs," Genes Dev, 2001, 15(2):188-200.

Elena et al., "Autoradiographic Localization of Beta-Adrenergic Receptors in Rabbit Eye," Investigative Ophthalmology & Visual Science, 28, pp. 1436-1441, Aug. 1987.

Epstein et al., "Effect of Iodoacetamide Perfusion on Outflow Facility and Metabolism of the Trabecular Meshwork," Invest. Ophthalmol. Vis. Sci., 625-631, May 1981.

Fattal et al., "Ocular Delivery of Nucleic Acids: Antisense Oligonucleotides, Aptamers and siRNA," Advanced Drug Delivery Reviews, 2006, 58:1203-1223.

Fire et al., "Potent and Specific Genetic Interference by Double Stranded RNA in a Caenorhabditis elegans," Nature, 1998, 391(6669):806-11.

Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.

Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.

Gil et al., "Induction of Apoptosis by the dsRNA-dependent Protein Kinase (PKR): Mechanism of Action," Apoptosis, 2000, 5(2):107-114.

Gonzalez et al., "Genes Upregulated in the Human Trabecular Meshwork in Response to Elevated Intraocular Pressure," Investigative Opthalmology & Visual Science, Feb. 2000, 41(2):352-361.

Grosshans et al., "Micro-RNAs: Small is Plentiful," J Cell Bioi, 2002, 156(1):17-21.

Grunweller et al., "Comparison of Different Antisense Strategies in Mammalian Cells Using Locked Nucleic Acids, 2' O-methyl RNA," Nucleic Acids Research, vol. 31, No. 12, pp. 3185-3193, Jun. 15, 2003.

Hammond et al., "Post-Transcriptional Gene Silencing by Double-Standed RNA," Nature, 2001, 2:110-119.

Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.

Herkel et al., "Update on Topical Carbonic Anhydrase Inhibitors," Current Opinion in Ophthamology, Apr. 2001, 12(2):88-93.

Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.

Horinouchi et al., "Pharmacological Evaluation of Ocular β-Adrenoceptors in Rabbit by Tissue Segment Binding Method," Life Sciences, 84, pp. 181-187, 2009.

Jens Kurreck, "Antisense Technologies," Eur. J. Biochem., 270, pp. 1628-1644, 2003.

Jens Kurreck, "Antisense and RNA Interference Approaches to Target Validation in Pain Research," Current Opinion in Drug Discovery & Development, 7(2), pp. 179-187, 2004.

Kaplan et al., "Aqueous Humor Flow in Unilateral Carotid Stenosis," Journal of Glaucoma, 5, pp. 237-240, 1996.

Khaw et al., "Glaucoma-1: Diagnosis," BMJ, 2004a, 328:97-99.

Khaw et al., "Glaucoma-2: Treatment," BMJ, 2004, 328:156-158.

Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.

Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.

Krutzfeldt et al., "Silencing of microRNAs in vivo with 'Antagomirs'," Nature, 2005, 438(7068):685-689.

Kwon et al., "Primary Open-Angle Glaucoma," The New England Journal of Medicine, 360(11), pp. 1113-1124, Mar. 12, 2009.

Lograno et al., "Receptor-Responses in Fresh Human Ciliary Muscle," Br. J. Pharmac., 87, pp. 379-385, 1986.

Madsen, "Ocular Finding in 123 Patients with Proliferative Diabetic Retinopathy," Documenta Ophthalmologica, Advances in ophthalmology, May 14, 1971, 29(2):345-349.

Mahato et al., "Modulation of Gene Expression by Antisense and Antigene Oligodeoxynucleotides and Small Interfering RNA," Expert Opinion on Drug Delivery, Jan. 2005, 2(1):3-28.

Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.

Miller et al., "Allele-specific Silencing of Dominant Disease Genes," Proceedings of the National Academy of Sciences of USA, Jun. 10, 2003, 100(12):7195-7200.

Muratovska et al., "Conjugate for Efficient Delivery of Short Interfering RNA (siRNA) into Mammalian Cells," FEBS Letters, 558, pp. 63-68, 2004.

Okabe et al., "Effect of Benzalkonium Chloride on Transscleral Drug Delivery," Investigative Ophthalmology & Visual Science, vol. 46, No. 2, pp. 703-708 , Feb. 2005.

Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.

Osborne et al., "Some Current Ideas on the Pathogenesis and the Role of Neuroprotection in Glaucomatous Optic Neuropathy," Eur J Ophthalmol., Apr. 2003, 13Suppl. 3:S19-26.

Paddison et al., "Short hairpin RNAs (shRNAs) Induce Sequence-Specific Silencing in Mammalian Cells," Genes Dev, 2002, 16(8):948-958.

Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.

Rao et al., "Modulation of Aqueous Humor Outflow Facility by the Rho Kinase-Specific Inhibitor Y-27632," Investigative Opthalmology & Visual Science, Apr. 2001, 42(5): 1029-1037.

Reich et al., "Small Interfering RNA (siRNA) Targeting *VEGF* effectively Inhibits Ocular Neovascularization in a Mouse Model," Molecular Vision, 2003, 9:210-216.

Sakaguchi et al., "Chymase and Angiotensin Converting Enzyme Activities in a Hamster Model of Glaucoma Filtering Surgery," Curr Eye Res., May 2002, 24(5):325-331.

Scherer et al., "Approaches for the Sequence-Specific Knockdown of mRNA," Nat. Biotechnology, 2003, 21(12):1457-1465.

Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.

Stamer et al., "Isolation and Culture of Human Trabecular Meshwork Cells by Extracellular Matrix Digestion," Current Eye Research, pp. 611-617, Jan. 10, 1995.

Tan et al., "Recent Developments in Understanding the Pathophysiology of Elevated Intraocular Pressure," Current Opinion in Opthalmology, vol. 17, pp. 168-174, 2006.

Tuschl et al., "Targeted mRNA degradation by double-stranded RNA in vitro," Genes Dev., 1999, 13(24):3191-3197.

Uprichard et al., The Therapeutic Potential of RNA Interference, FEBS Letters, Oct. 31, 2005 579(26):5996-6007.

U. Herkel et al, Update on topical carbonic anhydrase inhibitors, Curr. Opthalmol., vol. 12 (2), p. 88-93, Apr. 2001, XP002375306.

Valls et al., "Validation of a Device for Transcorneal Drug Permeation Measure," Journal of Pharmaceutical and Biomedical Analysis, 48, pp. 657-663, 2008.

Vittal et al., "Changes in Gene Expression by Trabecular Meshword Cells in Response to Mechanical Stretching," Investigative Opthalmology & Visual Science, Aug. 2005, 46(8):2857-2868.

Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan 4, 2005.

Wax et al., "Vacuolar $H^+$ -ATPase in Ocular Ciliary Epithelium," Proc. Natl. Acad. Sci., vol. 94, pp. 6752-6757, Jun. 1997.

Wetering et al., "Specific Inhibition of Gene Expression Using a Stably Integrated, Inducible Small-Interfering-RNA Vector," EMBO Reports, Jun. 2003, 4(6):609-615.

Wianny et al., "Specific Interference with Gene Function by Double-Stranded RNA in Early Mouse Development," Nat Cell Biol, 2000, 2(2):70-75.

Williams BR, "Role of the Double-Stranded RNA-activated Protein kinase (PKR) in Cell Regulation," Biochem Soc Trans, 1997, 25(2):509-513.

Wirtz et al., "The Genetic Loci of Open-Angle Glaucoma," Ophthalmol. Clin. North Am. 2003 16:505-514.

Wiznerowicz et al., "Conditional Suppression of Cellular Genes: Lentivirus Vector-Mediated Drug-Inducible RNA Interference," Journal of Virology, Aug. 2003, 77(16):8957-8961.

Woodward et al., "The Inflow and Outflow of Anti-Glaucoma Drugs," Trends in Pharmacological Sciences, May 2004, 25(5):238-241.

Xie et al., "Harnessing in vivo siRNA Delivery for Drug Discovery and Therapeutic Development," Drug Discovery Today, Jan. 2006, 11(1-2):67-73.

Yang-Feng et al., "Chromosomal Organization of Adrenergic Receptor Genes," PNAS, 1990, 87:1516-1520.

Yang et al., "Early Growth Response Gene 1 Modulates Androgen Receptor Signaling in Prostate Carcinoma Cells," The Journal of Biological Chemistry, 278(41), pp. 39906-39911, 2003.
Office Action dated Jul. 14, 2008 in corresponding U.S. Appl. No. 11/360,305.
Office Action dated Jan. 29, 2009 in corresponding U.S. Appl. No. 11/360,305.
Office Action dated Nov. 12, 2008 in corresponding U.S. Appl. No. 11/574,169.
Final Office Action dated May 8, 2009 in corresponding U.S. Appl. No. 11/574,169.
Office Action dated Nov. 3, 2009 in corresponding U.S. Appl. No. 12/170,078.
Office Action dated Oct. 15, 2009 in corresponding U.S. Appl. No. 12/170,104.
Office Action dated Oct. 15, 2009 in corresponding U.S. Appl. No. 12/170,157.
Office Action dated Oct. 30, 2009 in corresponding U.S. Appl. No. 12/170,116.
Office Action dated Oct. 30, 2009 in corresponding U.S. Appl. No. 12/170,132.
Office Action dated Oct. 19, 2009 in corresponding U.S. Appl. No. 12/170,148.
Office Action dated Dec. 4, 2009 in corresponding U.S. Appl. No. 11/574,169.
Office Action dated Mar. 19, 2010 in corresponding U.S. Appl. No. 12/170,078.
Office Action dated Mar. 22, 2010 in corresponding U.S. Appl. No. 12/170,104.
Office Action dated Mar. 19, 2010 in corresponding U.S. Appl. No. 12/170,116.
Office Action dated Mar. 22, 2010 in corresponding U.S. Appl. No. 12/170,132.
Office Action dated Mar. 22, 2010 in corresponding U.S. Appl. No. 12/170,148.
Office Action dated Mar. 22, 2010 in corresponding U.S. Appl. No. 12/170,157.
Office Action dated Mar. 25, 2010 in corresponding U.S. Appl. No. 12/563,530.
Final Office Action dated Jul. 22, 2010 in corresponding U.S. Appl. No. 11/574,169.
Office Action dated Sep. 7, 2010 in corresponding U.S. Appl. No. 11/574,169.
Office Action dated Mar. 22, 2010 in corresponding U.S. Appl. No. 12/170,530.
Office Action dated Sep. 23, 2010 in corresponding U.S. Appl. No. 12/170,078.
Office Action dated Sep. 23, 2010 in corresponding U.S. Appl. No. 12/170,104.
Office Action dated Sep. 23, 2010 in corresponding U.S. Appl. No. 12/170,116.
Office Action dated Sep. 23, 2010 in corresponding U.S. Appl. No. 12/170, 132.
Office Action dated Sep. 23, 2010 in corresponding U.S. Appl. No. 12/170,148.
Office Action dated Sep. 23, 2010 in corresponding U.S. Appl. No. 12/170,157.
Ahern et al., "Extracellular cations sensitize and gate capsaicin receptor TRPV1 modulating pain signaling", J. Neurosci. May 25, 2005;25(21):5109-16.
Akashi et al., "Suppression of gene expression by RNA interference in cultured plant cells", Antisense Nucleic Acid Drug Dev, 2001, 11(6):359).
Banerjee et al., "Control of developmental timing by small temporal RNAs: a paradigm for RNA-mediated regulation of gene expression", Bioessays, 2002, 24(2):119-29.
Basu et al., "Immunological role of neuronal receptor vanilloid receptor 1 expressed on dendritic cells", Proc Natl Acad Sci U S A. Apr. 5, 2005;102(14):5120-5. Epub Mar. 25, 2005
Baumann et al., "Extracellular protons both increase the activity and reduce the conductance of capsaicin-gated channels", J Neurosci. 2000;20:RC80.

Bodo et al., "A hot new twist to hair biology: involvement of vanilloid receptor-1 (VR1/TRPV1) signaling in human hair growth control", Am J Pathol. Apr. 2005;166(4):985-98.
Bosher et al., "RNA interference: genetic wand and genetic watchdog", Nat Cell Biol, 2000, 2(2):E31.
Brock et al., "Tetrodotoxin-resistant impulses in single nociceptor nerve terminals in guinea-pig cornea",. J Physiol. Oct. 1, 1998;512 ( Pt 1)211-7.
Brock et al., "Effects of Ca2+ and K+ channel blockers on nerve impulses recorded from postganglionic sympathetic nerve terminals", The Journal of Physiology, 1995, 489, 389-402.
Caplen et al., :Specific inhibition of gene expression by small double stranded RNAs in invertebrate and vertebrate systems, Proc. Natl. Acad. Sci. USA, 2001, 98: 9742.
Caterina et al., "The capsaicin receptor: a heat-activated ion channel in the pain pathway", Nature, Oct. 23, 1997;389(6653):816-24.
Caterina et al., "The vanilloid receptor: a molecular gateway to the pain pathway", Annu Rev Neurosci., 2001; 24:487-517.
Christoph et al., "RNA Interference approaches of target validation in pain research", International Society for Neurochemistry, Journal of Neurochemistry, 2005, vol. 94 (Suppl. 2), pp. 141.
Christoph et al., "Silencing of vanilloid receptor TRPV1 by RNAi reduces neuropathic and visceral pain in vivo", Biochemical and Biophysical Research Communications, 2006, vol. 350, pp. 238-243.
Di Marzo et al., "Endovanilloid signaling in pain", Curr Opin Neurobiol., Aug. 2002;12(4):372-9.
Elbashir et al., "RNA interference is mediated by 21- and 22-nucleotide RNAs", Genes Dev, 2001, 15(2):188.
Fire et al., "Potent and specific genetic interference by double stranded RNA in *Caenorhabditis elegans*", Nature, 1998, 391:806.
García-Martinez et al., "Attenuation of thermal nociception and hyperalgesia by VR1 blockers", Proc Natl Acad Sci U S A. Feb. 19, 2002;99(4):2374-9.
Gil et al., "Induction of apoptosis by the dsRNA-dependent protein kinase (PKR): mechanism of action", Apoptosis, 2000, 5(2):107-14).
Grant et al., "Insulin-like growth factors in vitreous. Studies in control and diabetic subjects with neovascularization", Diabetes, 1986; 35:416-420.
Grosshans et al., "Micro-RNAs: small is plentiful", J Cell Biol, 2002, 156(1):17.
Inokuchi et al., "Vitreous levels of insulin-like growth factor-I in patients with proliferative diabetic retinopathy", Curr. Eye Res., 2001; 23:368-371.
Jia et al., "TRPV1 receptor: a target for the treatment of pain, cough, airway disease and urinary incontinence", Drug News Perspect. Apr. 2005;18(3):165-71.
Lilja et al., "Development of a sensory neuronal cell model for the estimation of mild eye irritation", Altern Lab Anim. Oct. 2004;32(4):339-43.
Merimee et al., "Insulin-like growth factors. Studies in diabetics with and without retinopathy", N. Engl. J. Med., 1983; 309:527-530.
Meyer-Schwickerath et al., "Vitreous levels of the insulin-like growth factors I and II, and the insulin-like growth factor binding proteins 2 and 3, increase in neovascular eye disease—Studies in nondiabetic and diabetic subjects", J Clin Invest., 1993;92(6):2620-5.
Moriyama et al., "Sensitization of TRPV1 by EP1 and IP reveals peripheral nociceptive mechanism of prostaglandins", Mol Pain. Jan. 17, 2005;1(1):3.
Paddison et al, "Short hairpin RNAs (shRNAs) induce sequence-specific silencing in mammalian cells", Genes Dev, 2002, 16(8):948.
Ruberte et al., "Increased ocular levels of IGF-1 in transgenic mice lead to diabetes-like eye disease", J Clin Invest. Apr. 2004;113(8):1149-57.
Schubert et al., "Local RNA Target Structure Influences siRNA Efficacy: Systematic Analysis of Intentionally Designed Binding Regions", J. Mol. Biol., 2006, 348, pp. 883-893.
Stander et al., "Expression of vanilloid receptor subtype 1 in cutaneous sensory nerve fibers, mast cells, and epithelial cells of appendage structures", Exp Dermatol. Mar. 2004;13(3):129-39.
Van Buren et al., "Sensitization and translocation of TRPV1 by insulin and IGF-I", Mol Pain, Apr. 27, 2005;1(1):17.

Wianny et al., "Specific interference with gene function by double-stranded RNA in early mouse development", Nat Cell Biol, 2000, 2(2):70). Research at Ribopharma AG (Kulmbach, Germany).

Williams, B. R. G., "Role of the double-stranded RNA-activated protein kinase (PKR) in cell regulation", Biochem Soc Trans, 1997, 25(2):509.

International Search Report, International Preliminary Report on Patentability and Written Opinion for corresponding PCT Application No. PCT/GB2006/050342, mailed Apr. 24, 2007, 12 pages.

Gruenweller et al., "RNA Interference Approaches for Target Validation in Pain Research", Society for Neurochemistry, Journal of Neurochemistry, 2005, vol. 94 (Suppl. 2), pp. 141.

Liao et al., "Expression of Cell Surface Transmembrane Carbonic Anhydrase Genes CA9 and CA12 in the Human Eye: Overexpression of CA12 (CAXII) in Glaucoma," J. Med. Genet., 40:257-262, 2003.

Supuran et al., "Carbonic Anhydrase Inhibitors," Medicinal Research Reviews, 23(2):146-189, 2003.

Office Action dated Aug. 10, 2011, in corresponding U.S. Appl. No. 12/091,498.

Andrieu-Soler C., et al "Ocular gene therapy: A review of nonviral strategies," *Molecular Vision*, 12:1334-47, 2006.

Dejneka NS., et al., "Ocular Biodistribution of Bevasiranib Following a Single Intravitreal Injection to Rabbit Eyes," *Molecular Vision*, 14:997-1005, 2008.

Dos Santos ALG., et al "Intraocular Delivery of Oligonucleotides," *Current Pharmaceutical Biotechnology*, 6:7-15, 2005.

Flynn, "Efficient delivery of small interfering RNA for inhibition of IL-12p40 expression in vivo," J Inflamm (Lond), Oct. 1, 2004;1(1):4.

Jiménez et al., "Efficacy of Topically Administered siRNAs in Glaucoma Treatment: In vivo Results in Hypertensive Model," Investigative Ophthalmology & Visual Science, 50, E-Abstract 4054, 2009.

Jiménez et al., "Na+/K+ ATPase: A New Target for Treating Ocular Hypertension by RNAi," Investigative Ophthalmology & Visual Science, 48, E-Abstract 4809 2007.

Jiménez et al., "SYL04003; A New Therapeutic Candidate for Treating Ocular Hypertension using RNAi Technology," Investigative Ophthalmology & Visual Science, 49, E-Abstract 1643, 2008.

Jiménez et al., "SYL040012 A New siRNA-Based Treatment for Glaucoma: Pharmacokinetics and Mechanism of Action," Investigative Ophthalmology & Visual Science, 51, E-Abstract 176, 2010.

Peral et al., "Effect of Several siRNA in the Treatment of Ocular Hypertension and Glaucoma," Invest. Ophthalmol. Vis. Sci., 48, E-Abstract 4808, 2007.

Pintor et al., "SiRNA in the Treatment of Ocular Hypertension Targeting Alpha and Beta Adrenoceptors," Invest. Ophthalmol. Vis. Sci., 47, E-Abstract 403, 2006.

Ruz et al., "Phase I Study With a New siRNA: SYL040012. Tolerance and Effect on Intraocular Pressure," Investigative Ophthalmology Visual Science, 52, E-Abstract 223, 2011.

U.S. Appl. No. 12/091,498, filed Jun. 10, 2008, Ana Jimenez Anton.

Bujalska et al., "Hexose-6-phosphate Dehydrogenase Confers Oxo-Reductase Activity Upon 11beta-hydroxysteroid Dehydrogenase Type 1," Journal of Molecular Endocrinology, 34(3), pp. 675-684, Jun. 2005.

Davson H, "The Aqueous Humour and The Intraocular Pressure," Davson's Physiology of the Eye, 5th edition, Pergamon Press, pp. 3-95, 1990.

Hart WM, "Intraocular Pressure," Chapter 8, Adler's Physiology of the Eye: Clinical Application, Mosby-Year Book Inc., 9th edition, pp. 248-267, 1992.

Mirshahi et al., "The Mineralocorticoid Hormone Receptor and Action in the Eye," Biochem Biophys Res Commun, vol. 219, pp. 150-156, 1996.

Papers filed on Mar. 2, 2012, from opponents in Opposition by Alcon Research, Ltd. against Australian Patent Application No. 2005276245 in the name of Sylentis SAU.

Rauz et al., "Expression and Putative Role of 11beta-Hydroxysteriod Dehydrogenase Isozymes Within the Human Eye," Investigative Ophthalmology & Visual Science, 42(9), pp. 2037-2042, 2001.

Rauz at al., "Inhibition of 11beta-hydroxysteriod dehydrogenase type 1 Lowers Intraocular Pressure in Patients with Ocular Hypertension," 96(7), pp. 481-490, Jul. 2003.

Stokes et al., "Distribution of Glucocorticoid and Mineralocorticoid Receptors and 11 β-Hydroxysteroid Dehydrogenases in Human and Rat Ocular Tissues," Invest. Ophthalmol. Vis Sci., 41(7), pp. 1629-1638, Jun. 2000.

Studies conducted in the Biochemistry Department of the School of Optics at the Universidad Complutense de Madrid, as filed in the Information Disclosure Statement of Oct. 30, 2008 (in U.S. Appl. No. 11/574,169).

Suzuki et al., "Immunohistochemical Distribution of 11β-hydroxysteroid Dehydrogenase in Human Eye," Mol Cell Endocrinol, vol. 173, pp. 121-125, 2001.

Tomlinson, "11Beta-hydroxsteroid Dehydogenase Type I in Human Disease: a Novel Therapeutic Target," Minerva Endocrinologica, 30(1), Mar. 2005.

Office Action dated Mar. 19, 2012 in corresponding U.S. Appl. No. 12/170,104.

Office Action dated Mar. 19, 2012 in corresponding U.S. Appl. No. 12/170,116.

Office Action dated Mar. 19, 2012 in corresponding U.S. Appl. No. 12/170,132.

Office Action dated Mar. 19, 2012 in corresponding U.S. Appl. No. 12/170,148.

Office Action dated Mar. 19, 2012 in corresponding U.S. Appl. No. 12/170,157.

* cited by examiner

Figure 1A

| Transient receptor potential cation channel, subfamily V, member 1 (TRPV1) | |
|---|---|
| SEQ ID 1 | GAAATGGAGCAGCACAGAC |
| SEQ ID 2 | ATGGAGCAGCACAGACTTG |
| SEQ ID 3 | TGGAGCAGCACAGACTTGG |
| SEQ ID 4 | AAGGACACCTGCCCAGACC |
| SEQ ID 5 | GACCCTCAGGCTCTATGAT |
| SEQ ID 6 | GCCGTTGCTCAGAATAACT |
| SEQ ID 7 | TAACTGCCAGGATCTGGAG |
| SEQ ID 8 | CTGCCAGGATCTGGAGAGC |
| SEQ ID 9 | GAGCAAGAAGCACCTCACA |
| SEQ ID 10 | GAAGCACCTCACAGACAAC |
| SEQ ID 11 | GCACCTCACAGACAACGAG |
| SEQ ID 12 | CGAGTTCAAAGACCCTGAG |
| SEQ ID 13 | AGACCCTGAGACAGGGAAG |
| SEQ ID 14 | GACCCTGAGACAGGGAAGA |
| SEQ ID 15 | GACCTGTCTGCTGAAAGCC |
| SEQ ID 16 | AGCCATGCTCAACCTGCAT |
| SEQ ID 17 | GCCATGCTCAACCTGCATG |
| SEQ ID 18 | CCTGCATGACGGACAGAAC |
| SEQ ID 19 | ACGGACAGCCTGAAGGAGC |
| SEQ ID 20 | CGGACAGCCTGAAGGAGCT |
| SEQ ID 21 | GGAGCTTGTCAACGCCAGC |
| SEQ ID 22 | GAAAACCAAAGGGCGGCCT |
| SEQ ID 23 | AACCAAAGGGCGGCCTGGA |
| SEQ ID 24 | ACCAAAGGGCGGCCTGGAT |
| SEQ ID 25 | CCAAAGGGCGGCCTGGATT |
| SEQ ID 26 | AGGGCGGCCTGGATTCTAC |
| SEQ ID 27 | GGGCGGCCTGGATTCTACT |
| SEQ ID 28 | CCAGCTGGGCATCGTGAAG |
| SEQ ID 29 | GTTCCTGCTGCAGAACTCC |
| SEQ ID 30 | CACGGCCGACAACACGAAG |
| SEQ ID 31 | CACGAAGTTTGTGACGAGC |
| SEQ ID 32 | GTTTGTGACGAGCATGTAC |
| SEQ ID 33 | TGAGATTCTGATCCTGGGG |
| SEQ ID 34 | ACTGCACCCGACGCTGAAG |
| SEQ ID 35 | GCTGGAGGAGCTCACCAAC |
| SEQ ID 36 | CAAGAAGGGAATGACGCCG |
| SEQ ID 37 | GAAGGGAATGACGCCGCTG |
| SEQ ID 38 | GATCGGGGTCTTGGCCTAT |
| SEQ ID 39 | GTTCACCGAGTGGGCCTAC |
| SEQ ID 40 | GAACTCGGTGCTGGAGGTG |
| SEQ ID 41 | CTCGGTGCTGGAGGTGATC |
| SEQ ID 42 | TCGCCACGACATGCTCTTG |
| SEQ ID 43 | CCGACTCCTGCAGGACAAG |
| SEQ ID 44 | GTGGGACAGATTCGTCAAG |
| SEQ ID 45 | GCGCATCTTCTACTTCAAC |

Figure 1B

| SEQ ID 46 | CTTCCTGGTCTACTGCCTG |
| SEQ ID 47 | GATGGAAAAAATTGGAGAC |
| SEQ ID 48 | AAATTGGAGACTATTTCCG |
| SEQ ID 49 | AATTGGAGACTATTTCCGA |
| SEQ ID 50 | ATTGGAGACTATTTCCGAG |
| SEQ ID 51 | TTGGAGACTATTTCCGAGT |
| SEQ ID 52 | GACCCTGTTTGTGGACAGC |
| SEQ ID 53 | GGAGTATGTGGCTTCCATG |
| SEQ ID 54 | CATGCTCTACTACACCCGC |
| SEQ ID 55 | GATGATCCTGAGAGACCTG |
| SEQ ID 56 | GACGGGAAGAATGACTCCC |
| SEQ ID 57 | GAATGACTCCCTGCCGTCT |
| SEQ ID 58 | TGACTCCCTGCCGTCTGAG |
| SEQ ID 59 | CAGCCTGTACTCCACCTGC |
| SEQ ID 60 | GTTCACCATCGGCATGGGC |
| SEQ ID 61 | CTATGACTTCAAGGCTGTC |
| SEQ ID 62 | GGCTGTCTTCATCATCCTG |
| SEQ ID 63 | TTCTCACCTACATCCTCCT |
| SEQ ID 64 | CATGCTCATCGCCCTCATG |
| SEQ ID 65 | CAAGATCGCACAGGAGAGC |
| SEQ ID 66 | GATCGCACAGGAGAGCAAG |
| SEQ ID 67 | GAACATCTGGAAGCTGCAG |
| SEQ ID 68 | CATCTGGAAGCTGCAGAGA |
| SEQ ID 69 | GCTGCAGAGAGCCATCACC |
| SEQ ID 70 | GAGCTTCCTTAAGTGCATG |
| SEQ ID 71 | GTGCATGAGGAAGGCCTTC |
| SEQ ID 72 | CTGGACCACCTGGAACACC |
| SEQ ID 73 | CACCAACGTGGGCATCATC |
| SEQ ID 74 | CGTGGGCATCATCAACGAA |
| SEQ ID 75 | CGAAGACCCGGGCAACTGT |
| SEQ ID 76 | GCAGAGTTTCAGGCAGACA |
| SEQ ID 77 | GAACTTTGCCCTGGTCCCC |
| SEQ ID 78 | CTTTGCCCTGGTCCCCCTT |
| SEQ ID 79 | GAGAGGCAAGTGCTCGAGA |
| SEQ ID 80 | GTGCTCGAGATAGGCAGTC |
| SEQ ID 81 | GTTTATCTGCGACAGTTTT |

Figure 2A

| Transient receptor potential cation channel, subfamily V, member 1 (TRPV1) | |
|---|---|
| SEQ ID 82 | 5' GAAAUGGAGCAGCACAGAC 3'<br>\|\|\|\|\|\|\|\|\|\|\|\|\|\|\|\|\|\|\|<br>3' CUUUACCUCGUCGUGUCUG 5' |
| SEQ ID 83 | 5' AUGGAGCAGCACAGACUUG 3'<br>\|\|\|\|\|\|\|\|\|\|\|\|\|\|\|\|\|\|\|<br>3' UACCUCGUCGUGUCUGAAC 5' |
| SEQ ID 84 | 5' UGGAGCAGCACAGACUUGG 3'<br>\|\|\|\|\|\|\|\|\|\|\|\|\|\|\|\|\|\|\|<br>3' ACCUCGUCGUGUCUGAACC 5' |
| SEQ ID 85 | 5' AAGGACACCUGCCCAGACC 3'<br>\|\|\|\|\|\|\|\|\|\|\|\|\|\|\|\|\|\|\|<br>3' UUCCUGUGGACGGGUCUGG 5' |
| SEQ ID 86 | 5' GACCCUCAGGCUCUAUGAU 3'<br>\|\|\|\|\|\|\|\|\|\|\|\|\|\|\|\|\|\|\|<br>3' CUGGGAGUCCGAGAUACUA 5' |
| SEQ ID 87 | 5' GCCGUUGCUCAGAAUAACU 3'<br>\|\|\|\|\|\|\|\|\|\|\|\|\|\|\|\|\|\|\|<br>3' CGGCAACGAGUCUUAUUGA 5' |
| SEQ ID 88 | 5' UAACUGCCAGGAUCUGGAG 3'<br>\|\|\|\|\|\|\|\|\|\|\|\|\|\|\|\|\|\|\|<br>3' AUUGACGGUCCUAGACCUC 5' |
| SEQ ID 89 | 5' CUGCCAGGAUCUGGAGAGC 3'<br>\|\|\|\|\|\|\|\|\|\|\|\|\|\|\|\|\|\|\|<br>3' GACGGUCCUAGACCUCUCG 5' |
| SEQ ID 90 | 5' GAGCAAGAAGCACCUCACA 3'<br>\|\|\|\|\|\|\|\|\|\|\|\|\|\|\|\|\|\|\|<br>3' CUCGUUCUUCGUGGAGUGU 5' |
| SEQ ID 91 | 5' GAAGCACCUCACAGACAAC 3'<br>\|\|\|\|\|\|\|\|\|\|\|\|\|\|\|\|\|\|\|<br>3' CUUCGUGGAGUGUCUGUUG 5' |
| SEQ ID 92 | 5' GCACCUCACAGACAACGAG 3'<br>\|\|\|\|\|\|\|\|\|\|\|\|\|\|\|\|\|\|\|<br>3' CGUGGAGUGUCUGUUGCUC 5' |
| SEQ ID 93 | 5' CGAGUUCAAAGACCCUGAG 3'<br>\|\|\|\|\|\|\|\|\|\|\|\|\|\|\|\|\|\|\|<br>3' GCUCAAGUUUCUGGGACUC 5' |
| SEQ ID 94 | 5' AGACCCUGAGACAGGGAAG 3'<br>\|\|\|\|\|\|\|\|\|\|\|\|\|\|\|\|\|\|\|<br>3' UCUGGGACUCUGUCCCUUC 5' |
| SEQ ID 95 | 5' GACCCUGAGACAGGGAAGA 3'<br>\|\|\|\|\|\|\|\|\|\|\|\|\|\|\|\|\|\|\|<br>3' CUGGGACUCUGUCCCUUCU 5' |
| SEQ ID 96 | 5' GACCUGUCUGCUGAAAGCC 3'<br>\|\|\|\|\|\|\|\|\|\|\|\|\|\|\|\|\|\|\|<br>3' CUGGACAGACGACUUUCGG 5' |
| SEQ ID 97 | 5' AGCCAUGCUCAACCUGCAU 3'<br>\|\|\|\|\|\|\|\|\|\|\|\|\|\|\|\|\|\|\|<br>3' UCGGUACGAGUUGGACGUA 5' |
| SEQ ID 98 | 5' GCCAUGCUCAACCUGCAUG 3'<br>\|\|\|\|\|\|\|\|\|\|\|\|\|\|\|\|\|\|\|<br>3' CGGUACGAGUUGGACGUAC 5' |
| SEQ ID 99 | 5' CCUGCAUGACGGACAGAAC 3'<br>\|\|\|\|\|\|\|\|\|\|\|\|\|\|\|\|\|\|\|<br>3' GGACGUACUGCCUGUCUUG 5' |
| SEQ ID 100 | 5' ACGGACAGCCUGAAGGAGC 3'<br>\|\|\|\|\|\|\|\|\|\|\|\|\|\|\|\|\|\|\|<br>3' UGCCUGUCGGACUUCCUCG 5' |
| SEQ ID 101 | 5' CGGACAGCCUGAAGGAGCU 3'<br>\|\|\|\|\|\|\|\|\|\|\|\|\|\|\|\|\|\|\|<br>3' GCCUGUCGGACUUCCUCGA 5' |
| SEQ ID 102 | 5' GGAGCUUGUCAACGCCAGC 3'<br>\|\|\|\|\|\|\|\|\|\|\|\|\|\|\|\|\|\|\|<br>3' CCUCGAACAGUUGCGGUCG 5' |
| SEQ ID 103 | 5' GAAAACCAAAGGGCGGCCU 3'<br>\|\|\|\|\|\|\|\|\|\|\|\|\|\|\|\|\|\|\|<br>3' CUUUUGGUUUCCCGCCGGA 5' |

Figure 2B

| | |
|---|---|
| SEQ ID 104 | 5' AACCAAAGGGCGGCCUGGA 3'<br>\|\|\|\|\|\|\|\|\|\|\|\|\|\|\|\|\|\|\|<br>3' UUGGUUUCCCGCCGGACCU 5' |
| SEQ ID 105 | 5' ACCAAAGGGCGGCCUGGAU 3'<br>\|\|\|\|\|\|\|\|\|\|\|\|\|\|\|\|\|\|\|<br>3' UGGUUUCCCGCCGGACCUA 5' |
| SEQ ID 106 | 5' CCAAAGGGCGGCCUGGAUU 3'<br>\|\|\|\|\|\|\|\|\|\|\|\|\|\|\|\|\|\|\|<br>3' GGUUUCCCGCCGGACCUAA 5' |
| SEQ ID 107 | 5' AGGGCGGCCUGGAUUCUAC 3'<br>\|\|\|\|\|\|\|\|\|\|\|\|\|\|\|\|\|\|\|<br>3' UCCCGCCGGACCUAAGAUG 5' |
| SEQ ID 108 | 5' GGGCGGCCUGGAUUCUACU 3'<br>\|\|\|\|\|\|\|\|\|\|\|\|\|\|\|\|\|\|\|<br>3' CCCGCCGGACCUAAGAUGA 5' |
| SEQ ID 109 | 5' CCAGCUGGGCAUCGUGAAG 3'<br>\|\|\|\|\|\|\|\|\|\|\|\|\|\|\|\|\|\|\|<br>3' GGUCGACCCGUAGCACUUC 5' |
| SEQ ID 110 | 5' GUUCCUGCUGCAGAACUCC 3'<br>\|\|\|\|\|\|\|\|\|\|\|\|\|\|\|\|\|\|\|<br>3' CAAGGACGACGUCUUGAGG 5' |
| SEQ ID 111 | 5' CACGGCCGACAACACGAAG 3'<br>\|\|\|\|\|\|\|\|\|\|\|\|\|\|\|\|\|\|\|<br>3' GUGCCGGCUGUUGUGCUUC 5' |
| SEQ ID 112 | 5' CACGAAGUUUGUGACGAGC 3'<br>\|\|\|\|\|\|\|\|\|\|\|\|\|\|\|\|\|\|\|<br>3' GUGCUUCAAACACUGCUCG 5' |
| SEQ ID 113 | 5' GUUUGUGACGAGCAUGUAC 3'<br>\|\|\|\|\|\|\|\|\|\|\|\|\|\|\|\|\|\|\|<br>3' CAAACACUGCUCGUACAUG 5' |
| SEQ ID 114 | 5' UGAGAUUCUGAUCCUGGGG 3'<br>\|\|\|\|\|\|\|\|\|\|\|\|\|\|\|\|\|\|\|<br>3' ACUCUAAGACUAGGACCCC 5' |
| SEQ ID 115 | 5' ACUGCACCCGACGCUGAAG 3'<br>\|\|\|\|\|\|\|\|\|\|\|\|\|\|\|\|\|\|\|<br>3' UGACGUGGGCUGCGACUUC 5' |
| SEQ ID 116 | 5' GCUGGAGGAGCUCACCAAC 3'<br>\|\|\|\|\|\|\|\|\|\|\|\|\|\|\|\|\|\|\|<br>3' CGACCUCCUCGAGUGGUUG 5' |
| SEQ ID 117 | 5' CAAGAAGGGAAUGACGCCG 3'<br>\|\|\|\|\|\|\|\|\|\|\|\|\|\|\|\|\|\|\|<br>3' GUUCUUCCCUUACUGCGGC 5' |
| SEQ ID 118 | 5' GAAGGGAAUGACGCCGCUG 3'<br>\|\|\|\|\|\|\|\|\|\|\|\|\|\|\|\|\|\|\|<br>3' CUUCCCUUACUGCGGCGAC 5' |
| SEQ ID 119 | 5' GAUCGGGGUCUUGGCCUAU 3'<br>\|\|\|\|\|\|\|\|\|\|\|\|\|\|\|\|\|\|\|<br>3' CUAGCCCCAGAACCGGAUA 5' |
| SEQ ID 120 | 5' GUUCACCGAGUGGGCUAC 3'<br>\|\|\|\|\|\|\|\|\|\|\|\|\|\|\|\|\|\|\|<br>3' CAAGUGGCUCACCCGGAUG 5' |
| SEQ ID 121 | 5' GAACUCGGUGCUGGAGGUG 3'<br>\|\|\|\|\|\|\|\|\|\|\|\|\|\|\|\|\|\|\|<br>3' CUUGAGCCACGACCUCCAC 5' |
| SEQ ID 122 | 5' CUCGGUGCUGGAGGUGAUC 3'<br>\|\|\|\|\|\|\|\|\|\|\|\|\|\|\|\|\|\|\|<br>3' GAGCCACGACCUCCACUAG 5' |
| SEQ ID 123 | 5' UCGCCACGACAUGCUCUUG 3'<br>\|\|\|\|\|\|\|\|\|\|\|\|\|\|\|\|\|\|\|<br>3' AGCGGUGCUGUACGAGAAC 5' |
| SEQ ID 124 | 5' CCGACUCCUGCAGGACAAG 3'<br>\|\|\|\|\|\|\|\|\|\|\|\|\|\|\|\|\|\|\|<br>3' GGCUGAGGACGUCCUGUUC 5' |
| SEQ ID 125 | 5' GUGGGACAGAUUCGUCAAG 3'<br>\|\|\|\|\|\|\|\|\|\|\|\|\|\|\|\|\|\|\|<br>3' CACCCUGUCUAAGCAGUUC 5' |
| SEQ ID 126 | 5' GCGCAUCUUCUACUUCAAC 3'<br>\|\|\|\|\|\|\|\|\|\|\|\|\|\|\|\|\|\|\|<br>3' CGCGUAGAAGAUGAAGUUG 5' |
| SEQ ID 127 | 5' CUUCCUGGUCUACUGCCUG 3'<br>\|\|\|\|\|\|\|\|\|\|\|\|\|\|\|\|\|\|\|<br>3' GAAGGACCAGAUGACGGAC 5' |

Figure 2C

| | | |
|---|---|---|
| SEQ ID 128 | 5' GAUGGAAAAAAUUGGAGAC 3'<br>\|\|\|\|\|\|\|\|\|\|\|\|\|\|\|\|\|\|\|<br>3' CUACCUUUUUUAACCUCUG 5' | |
| SEQ ID 129 | 5' AAAUUGGAGACUAUUUCCG 3'<br>\|\|\|\|\|\|\|\|\|\|\|\|\|\|\|\|\|\|\|<br>3' UUUAACCUCUGAUAAAGGC 5' | |
| SEQ ID 130 | 5' AAUUGGAGACUAUUUCCGA 3'<br>\|\|\|\|\|\|\|\|\|\|\|\|\|\|\|\|\|\|\|<br>3' UUAACCUCUGAUAAAGGCU 5' | |
| SEQ ID 131 | 5' AUUGGAGACUAUUUCCGAG 3'<br>\|\|\|\|\|\|\|\|\|\|\|\|\|\|\|\|\|\|\|<br>3' UAACCUCUGAUAAAGGCUC 5' | |
| SEQ ID 132 | 5' UUGGAGACUAUUUCCGAGU 3'<br>\|\|\|\|\|\|\|\|\|\|\|\|\|\|\|\|\|\|\|<br>3' AACCUCUGAUAAAGGCUCA 5' | |
| SEQ ID 133 | 5' GACCCUGUUUGUGGACAGC 3'<br>\|\|\|\|\|\|\|\|\|\|\|\|\|\|\|\|\|\|\|<br>3' CUGGGACAAACACCUGUCG 5' | |
| SEQ ID 134 | 5' GGAGUAUGUGGCUUCCAUG 3'<br>\|\|\|\|\|\|\|\|\|\|\|\|\|\|\|\|\|\|\|<br>3' CCUCAUACACCGAAGGUAC 5' | |
| SEQ ID 135 | 5' CAUGCUCUACUACACCCGC 3'<br>\|\|\|\|\|\|\|\|\|\|\|\|\|\|\|\|\|\|\|<br>3' GUACGAGAUGAUGUGGGCG 5' | |
| SEQ ID 136 | 5' GAUGAUCCUGAGAGACCUG 3'<br>\|\|\|\|\|\|\|\|\|\|\|\|\|\|\|\|\|\|\|<br>3' CUACUAGGACUCUCUGGAC 5' | |
| SEQ ID 137 | 5' GACGGAAGAAUGACUCCC 3'<br>\|\|\|\|\|\|\|\|\|\|\|\|\|\|\|\|\|\|\|<br>3' CUGCCCUUCUUACUGAGGG 5' | |
| SEQ ID 138 | 5' GAAUGACUCCCUGCCGUCU 3'<br>\|\|\|\|\|\|\|\|\|\|\|\|\|\|\|\|\|\|\|<br>3' CUUACUGAGGGACGGCAGA 5' | |
| SEQ ID 139 | 5' UGACUCCCUGCCGUCUGAG 3'<br>\|\|\|\|\|\|\|\|\|\|\|\|\|\|\|\|\|\|\|<br>3' ACUGAGGGACGGCAGACUC 5' | |
| SEQ ID 140 | 5' CAGCCUGUACUCCACCUGC 3'<br>\|\|\|\|\|\|\|\|\|\|\|\|\|\|\|\|\|\|\|<br>3' GUCGGACAUGAGGUGGACG 5' | |
| SEQ ID 141 | 5' GUUCACCAUCGGCAUGGGC 3'<br>\|\|\|\|\|\|\|\|\|\|\|\|\|\|\|\|\|\|\|<br>3' CAAGUGGUAGCCGUACCCG 5' | |
| SEQ ID 142 | 5' CUAUGACUUCAAGGCUGUC 3'<br>\|\|\|\|\|\|\|\|\|\|\|\|\|\|\|\|\|\|\|<br>3' GAUACUGAAGUUCCGACAG 5' | |
| SEQ ID 143 | 5' GGCUGUCUUCAUCAUCCUG 3'<br>\|\|\|\|\|\|\|\|\|\|\|\|\|\|\|\|\|\|\|<br>3' CCGACAGAAGUAGUAGGAC 5' | |
| SEQ ID 144 | 5' UUCUCACCUACAUCCUCCU 3'<br>\|\|\|\|\|\|\|\|\|\|\|\|\|\|\|\|\|\|\|<br>3' AAGAGUGGAUGUAGGAGGA 5' | |
| SEQ ID 145 | 5' CAUGCUCAUCGCCCUCAUG 3'<br>\|\|\|\|\|\|\|\|\|\|\|\|\|\|\|\|\|\|\|<br>3' GUACGAGUAGCGGGAGUAC 5' | |
| SEQ ID 146 | 5' CAAGAUCGCACAGGAGAGC 3'<br>\|\|\|\|\|\|\|\|\|\|\|\|\|\|\|\|\|\|\|<br>3' GUUCUAGCGUGUCCUCUCG 5' | |
| SEQ ID 147 | 5' GAUCGCACAGGAGAGCAAG 3'<br>\|\|\|\|\|\|\|\|\|\|\|\|\|\|\|\|\|\|\|<br>3' CUAGCGUGUCCUCUCGUUC 5' | |
| SEQ ID 148 | 5' GAACAUCUGGAAGCUGCAG 3'<br>\|\|\|\|\|\|\|\|\|\|\|\|\|\|\|\|\|\|\|<br>3' CUUGUAGACCUUCGACGUC 5' | |
| SEQ ID 149 | 5' CAUCUGGAAGCUGCAGAGA 3'<br>\|\|\|\|\|\|\|\|\|\|\|\|\|\|\|\|\|\|\|<br>3' GUAGACCUUCGACGUCUCU 5' | |
| SEQ ID 150 | 5' GCUGCAGAGAGCCAUCACC 3'<br>\|\|\|\|\|\|\|\|\|\|\|\|\|\|\|\|\|\|\|<br>3' CGACGUCUCUCGGUAGUGG 5' | |
| SEQ ID 151 | 5' GAGCUUCCUUAAGUGCAUG 3'<br>\|\|\|\|\|\|\|\|\|\|\|\|\|\|\|\|\|\|\|<br>3' CUCGAAGGAAUUCACGUAC 5' | |
| SEQ ID 152 | 5' GUGCAUGAGGAAGGCCUUC 3'<br>\|\|\|\|\|\|\|\|\|\|\|\|\|\|\|\|\|\|\| | |

Figure 2D

```
                        |||||||||||||||||||
                     3' CACGUACUCCUUCCGGAAG 5'
                     5' CUGGACCACCUGGAACACC 3'
SEQ ID 153              |||||||||||||||||||
                     3' GACCUGGUGGACCUUGUGG 5'
                     5' CACCAACGUGGGCAUCAUC 3'
SEQ ID 154              |||||||||||||||||||
                     3' GUGGUUGCACCCGUAGUAG 5'
                     5' CGUGGGCAUCAUCAACGAA 3'
SEQ ID 155              |||||||||||||||||||
                     3' GCACCCGUAGUAGUUGCUU 5'

5' CGAAGACCCGGGCAACUGU 3'
SEQ ID 156              |||||||||||||||||||
                     3' GCUUCUGGGCCCGUUGACA 5'
                     5' GCAGAGUUUCAGGCAGACA 3'
SEQ ID 157              |||||||||||||||||||
                     3' CGUCUCAAAGUCCGUCUGU 5'
                     5' GAACUUUGCCCUGGUCCCC 3'
SEQ ID 158              |||||||||||||||||||
                     3' CUUGAAACGGGACCAGGGG 5'
                     5' CUUUGCCCUGGUCCCCCUU 3'
SEQ ID 159              |||||||||||||||||||
                     3' GAAACGGGACCAGGGGGAA 5'
                     5' GAGAGGCAAGUGCUCGAGA 3'
SEQ ID 160              |||||||||||||||||||
                     3' CUCUCCGUUCACGAGCUCU 5'
                     5' GUGCUCGAGAUAGGCAGUC 3'
SEQ ID 161              |||||||||||||||||||
                     3' CACGAGCUCUAUCCGUCAG 5'
                     5' GUUUAUCUGCGACAGUUUU 3'
SEQ ID 162              |||||||||||||||||||
                     3' CAAAUAGACGCUGUCAAAA 5'
```

Stimulation:
- Mechanical: von Frey hairs
- Chemical: $CO_2$ pulse
- Thermal (heat): 45°C solution
- Capsaicin 0.1mM

SEQUENCE LISTING

<160> NUMBER OF SEQ ID NOS: 162

<210> SEQ ID NO 1
<211> LENGTH: 19
<212> TYPE: DNA
<213> ORGANISM: Homo sapiens

<400> SEQUENCE: 1
gaaatggagc agcacagac                                                19

<210> SEQ ID NO 2
<211> LENGTH: 19
<212> TYPE: DNA

<213> ORGANISM: Homo sapiens

<400> SEQUENCE: 2
atggagcagc acagacttg                                                  19

<210> SEQ ID NO 3
<211> LENGTH: 19
<212> TYPE: DNA
<213> ORGANISM: Homo sapiens

<400> SEQUENCE: 3
tggagcagca cagacttgg                                                  19

<210> SEQ ID NO 4
<211> LENGTH: 19
<212> TYPE: DNA
<213> ORGANISM: Homo sapiens

<400> SEQUENCE: 4
aaggacacct gcccagacc                                                  19

<210> SEQ ID NO 5
<211> LENGTH: 19
<212> TYPE: DNA
<213> ORGANISM: Homo sapiens

<400> SEQUENCE: 5
gaccctcagg ctctatgat                                                  19

<210> SEQ ID NO 6
<211> LENGTH: 19
<212> TYPE: DNA
<213> ORGANISM: Homo sapiens

<400> SEQUENCE: 6
gccgttgctc agaataact                                                  19

<210> SEQ ID NO 7
<211> LENGTH: 19
<212> TYPE: DNA
<213> ORGANISM: Homo sapiens

<400> SEQUENCE: 7
taactgccag gatctggag                                                  19

<210> SEQ ID NO 8
<211> LENGTH: 19
<212> TYPE: DNA
<213> ORGANISM: Homo sapiens

<400> SEQUENCE: 8
ctgccaggat ctggagagc                                                  19

<210> SEQ ID NO 9
<211> LENGTH: 19
<212> TYPE: DNA
<213> ORGANISM: Homo sapiens

<400> SEQUENCE: 9
gagcaagaag cacctcaca                                                  19

<210> SEQ ID NO 10
<211> LENGTH: 19
<212> TYPE: DNA

<213> ORGANISM: Homo sapiens

<400> SEQUENCE: 10
gaagcacctc acagacaac                                            19

<210> SEQ ID NO 11
<211> LENGTH: 19
<212> TYPE: DNA
<213> ORGANISM: Homo sapiens

<400> SEQUENCE: 11
gcacctcaca gacaacgag                                            19

<210> SEQ ID NO 12
<211> LENGTH: 19
<212> TYPE: DNA
<213> ORGANISM: Homo sapiens

<400> SEQUENCE: 12
cgagttcaaa gaccctgag                                            19

<210> SEQ ID NO 13
<211> LENGTH: 19
<212> TYPE: DNA
<213> ORGANISM: Homo sapiens

<400> SEQUENCE: 13
agaccctgag acagggaag                                            19

<210> SEQ ID NO 14
<211> LENGTH: 19
<212> TYPE: DNA
<213> ORGANISM: Homo sapiens

<400> SEQUENCE: 14
gaccctgaga cagggaaga                                            19

<210> SEQ ID NO 15
<211> LENGTH: 19
<212> TYPE: DNA
<213> ORGANISM: Homo sapiens

<400> SEQUENCE: 15
gacctgtctg ctgaaagcc                                            19

<210> SEQ ID NO 16
<211> LENGTH: 19
<212> TYPE: DNA
<213> ORGANISM: Homo sapiens

<400> SEQUENCE: 16
agccatgctc aacctgcat                                            19

<210> SEQ ID NO 17
<211> LENGTH: 19
<212> TYPE: DNA
<213> ORGANISM: Homo sapiens

<400> SEQUENCE: 17
gccatgctca acctgcatg                                            19

<210> SEQ ID NO 18
<211> LENGTH: 19
<212> TYPE: DNA

-continued

<213> ORGANISM: Homo sapiens

<400> SEQUENCE: 18
cctgcatgac ggacagaac                                               19

<210> SEQ ID NO 19
<211> LENGTH: 19
<212> TYPE: DNA
<213> ORGANISM: Homo sapiens

<400> SEQUENCE: 19
acggacagcc tgaaggagc                                               19

<210> SEQ ID NO 20
<211> LENGTH: 19
<212> TYPE: DNA
<213> ORGANISM: Homo sapiens

<400> SEQUENCE: 20
cggacagcct gaaggagct                                               19

<210> SEQ ID NO 21
<211> LENGTH: 19
<212> TYPE: DNA
<213> ORGANISM: Homo sapiens

<400> SEQUENCE: 21
ggagcttgtc aacgccagc                                               19

<210> SEQ ID NO 22
<211> LENGTH: 19
<212> TYPE: DNA
<213> ORGANISM: Homo sapiens

<400> SEQUENCE: 22
gaaaaccaaa gggcggcct                                               19

<210> SEQ ID NO 23
<211> LENGTH: 19
<212> TYPE: DNA
<213> ORGANISM: Homo sapiens

<400> SEQUENCE: 23
aaccaaaggg cggcctgga                                               19

<210> SEQ ID NO 24
<211> LENGTH: 19
<212> TYPE: DNA
<213> ORGANISM: Homo sapiens

<400> SEQUENCE: 24
accaaagggc ggcctggat                                               19

<210> SEQ ID NO 25
<211> LENGTH: 19
<212> TYPE: DNA
<213> ORGANISM: Homo sapiens

<400> SEQUENCE: 25
ccaaagggcg gcctggatt                                               19

<210> SEQ ID NO 26
<211> LENGTH: 19
<212> TYPE: DNA

<213> ORGANISM: Homo sapiens

<400> SEQUENCE: 26
agggcggcct ggattctac                                                    19

<210> SEQ ID NO 27
<211> LENGTH: 19
<212> TYPE: DNA
<213> ORGANISM: Homo sapiens

<400> SEQUENCE: 27
gggcggcctg gattctact                                                    19

<210> SEQ ID NO 28
<211> LENGTH: 19
<212> TYPE: DNA
<213> ORGANISM: Homo sapiens

<400> SEQUENCE: 28
ccagctgggc atcgtgaag                                                    19

<210> SEQ ID NO 29
<211> LENGTH: 19
<212> TYPE: DNA
<213> ORGANISM: Homo sapiens

<400> SEQUENCE: 29
gttcctgctg cagaactcc                                                    19

<210> SEQ ID NO 30
<211> LENGTH: 19
<212> TYPE: DNA
<213> ORGANISM: Homo sapiens

<400> SEQUENCE: 30
cacggccgac aacacgaag                                                    19

<210> SEQ ID NO 31
<211> LENGTH: 19
<212> TYPE: DNA
<213> ORGANISM: Homo sapiens

<400> SEQUENCE: 31
cacgaagttt gtgacgagc                                                    19

<210> SEQ ID NO 32
<211> LENGTH: 19
<212> TYPE: DNA
<213> ORGANISM: Homo sapiens

<400> SEQUENCE: 32
gtttgtgacg agcatgtac                                                    19

<210> SEQ ID NO 33
<211> LENGTH: 19
<212> TYPE: DNA
<213> ORGANISM: Homo sapiens

<400> SEQUENCE: 33
tgagattctg atcctgggg                                                    19

<210> SEQ ID NO 34
<211> LENGTH: 19
<212> TYPE: DNA

<213> ORGANISM: Homo sapiens

<400> SEQUENCE: 34
actgcacccg acgctgaag                                                    19

<210> SEQ ID NO 35
<211> LENGTH: 19
<212> TYPE: DNA
<213> ORGANISM: Homo sapiens

<400> SEQUENCE: 35
gctggaggag ctcaccaac                                                    19

<210> SEQ ID NO 36
<211> LENGTH: 19
<212> TYPE: DNA
<213> ORGANISM: Homo sapiens

<400> SEQUENCE: 36
caagaaggga atgacgccg                                                    19

<210> SEQ ID NO 37
<211> LENGTH: 19
<212> TYPE: DNA
<213> ORGANISM: Homo sapiens

<400> SEQUENCE: 37
gaagggaatg acgccgctg                                                    19

<210> SEQ ID NO 38
<211> LENGTH: 19
<212> TYPE: DNA
<213> ORGANISM: Homo sapiens

<400> SEQUENCE: 38
gatcggggtc ttggcctat                                                    19

<210> SEQ ID NO 39
<211> LENGTH: 19
<212> TYPE: DNA
<213> ORGANISM: Homo sapiens

<400> SEQUENCE: 39
gttcaccgag tgggcctac                                                    19

<210> SEQ ID NO 40
<211> LENGTH: 19
<212> TYPE: DNA
<213> ORGANISM: Homo sapiens

<400> SEQUENCE: 40
gaactcggtg ctggaggtg                                                    19

<210> SEQ ID NO 41
<211> LENGTH: 19
<212> TYPE: DNA
<213> ORGANISM: Homo sapiens

<400> SEQUENCE: 41
ctcggtgctg gaggtgatc                                                    19

<210> SEQ ID NO 42
<211> LENGTH: 19
<212> TYPE: DNA

<213> ORGANISM: Homo sapiens

<400> SEQUENCE: 42
tcgccacgac atgctcttg                                                19

<210> SEQ ID NO 43
<211> LENGTH: 19
<212> TYPE: DNA
<213> ORGANISM: Homo sapiens

<400> SEQUENCE: 43
ccgactcctg caggacaag                                                19

<210> SEQ ID NO 44
<211> LENGTH: 19
<212> TYPE: DNA
<213> ORGANISM: Homo sapiens

<400> SEQUENCE: 44
gtgggacaga ttcgtcaag                                                19

<210> SEQ ID NO 45
<211> LENGTH: 19
<212> TYPE: DNA
<213> ORGANISM: Homo sapiens

<400> SEQUENCE: 45
gcgcatcttc tacttcaac                                                19

<210> SEQ ID NO 46
<211> LENGTH: 19
<212> TYPE: DNA
<213> ORGANISM: Homo sapiens

<400> SEQUENCE: 46
cttcctggtc tactgcctg                                                19

<210> SEQ ID NO 47
<211> LENGTH: 19
<212> TYPE: DNA
<213> ORGANISM: Homo sapiens

<400> SEQUENCE: 47
gatggaaaaa attggagac                                                19

<210> SEQ ID NO 48
<211> LENGTH: 19
<212> TYPE: DNA
<213> ORGANISM: Homo sapiens

<400> SEQUENCE: 48
aaattggaga ctatttccg                                                19

<210> SEQ ID NO 49
<211> LENGTH: 19
<212> TYPE: DNA
<213> ORGANISM: Homo sapiens

<400> SEQUENCE: 49
aattggagac tatttccga                                                19

<210> SEQ ID NO 50
<211> LENGTH: 19
<212> TYPE: DNA

<213> ORGANISM: Homo sapiens

<400> SEQUENCE: 50
attggagact atttccgag                                                   19

<210> SEQ ID NO 51
<211> LENGTH: 19
<212> TYPE: DNA
<213> ORGANISM: Homo sapiens

<400> SEQUENCE: 51
ttggagacta tttccgagt                                                   19

<210> SEQ ID NO 52
<211> LENGTH: 19
<212> TYPE: DNA
<213> ORGANISM: Homo sapiens

<400> SEQUENCE: 52
gaccctgttt gtggacagc                                                   19

<210> SEQ ID NO 53
<211> LENGTH: 19
<212> TYPE: DNA
<213> ORGANISM: Homo sapiens

<400> SEQUENCE: 53
ggagtatgtg gcttccatg                                                   19

<210> SEQ ID NO 54
<211> LENGTH: 19
<212> TYPE: DNA
<213> ORGANISM: Homo sapiens

<400> SEQUENCE: 54
catgctctac tacacccgc                                                   19

<210> SEQ ID NO 55
<211> LENGTH: 19
<212> TYPE: DNA
<213> ORGANISM: Homo sapiens

<400> SEQUENCE: 55
gatgatcctg agagacctg                                                   19

<210> SEQ ID NO 56
<211> LENGTH: 19
<212> TYPE: DNA
<213> ORGANISM: Homo sapiens

<400> SEQUENCE: 56
gacgggaaga atgactccc                                                   19

<210> SEQ ID NO 57
<211> LENGTH: 19
<212> TYPE: DNA
<213> ORGANISM: Homo sapiens

<400> SEQUENCE: 57
gaatgactcc ctgccgtct                                                   19

<210> SEQ ID NO 58
<211> LENGTH: 19
<212> TYPE: DNA

<213> ORGANISM: Homo sapiens

<400> SEQUENCE: 58
tgactccctg ccgtctgag                                                19

<210> SEQ ID NO 59
<211> LENGTH: 19
<212> TYPE: DNA
<213> ORGANISM: Homo sapiens

<400> SEQUENCE: 59
cagcctgtac tccacctgc                                                19

<210> SEQ ID NO 60
<211> LENGTH: 19
<212> TYPE: DNA
<213> ORGANISM: Homo sapiens

<400> SEQUENCE: 60
gttcaccatc ggcatgggc                                                19

<210> SEQ ID NO 61
<211> LENGTH: 19
<212> TYPE: DNA
<213> ORGANISM: Homo sapiens

<400> SEQUENCE: 61
ctatgacttc aaggctgtc                                                19

<210> SEQ ID NO 62
<211> LENGTH: 19
<212> TYPE: DNA
<213> ORGANISM: Homo sapiens

<400> SEQUENCE: 62
ggctgtcttc atcatcctg                                                19

<210> SEQ ID NO 63
<211> LENGTH: 19
<212> TYPE: DNA
<213> ORGANISM: Homo sapiens

<400> SEQUENCE: 63
ttctcaccta catcctcct                                                19

<210> SEQ ID NO 64
<211> LENGTH: 19
<212> TYPE: DNA
<213> ORGANISM: Homo sapiens

<400> SEQUENCE: 64
catgctcatc gccctcatg                                                19

<210> SEQ ID NO 65
<211> LENGTH: 19
<212> TYPE: DNA
<213> ORGANISM: Homo sapiens

<400> SEQUENCE: 65
caagatcgca caggagagc                                                19

<210> SEQ ID NO 66
<211> LENGTH: 19
<212> TYPE: DNA

<213> ORGANISM: Homo sapiens

<400> SEQUENCE: 66
gatcgcacag gagagcaag                    19

<210> SEQ ID NO 67
<211> LENGTH: 19
<212> TYPE: DNA
<213> ORGANISM: Homo sapiens

<400> SEQUENCE: 67
gaacatctgg aagctgcag                    19

<210> SEQ ID NO 68
<211> LENGTH: 19
<212> TYPE: DNA
<213> ORGANISM: Homo sapiens

<400> SEQUENCE: 68
catctggaag ctgcagaga                    19

<210> SEQ ID NO 69
<211> LENGTH: 19
<212> TYPE: DNA
<213> ORGANISM: Homo sapiens

<400> SEQUENCE: 69
gctgcagaga gccatcacc                    19

<210> SEQ ID NO 70
<211> LENGTH: 19
<212> TYPE: DNA
<213> ORGANISM: Homo sapiens

<400> SEQUENCE: 70
gagcttcctt aagtgcatg                    19

<210> SEQ ID NO 71
<211> LENGTH: 19
<212> TYPE: DNA
<213> ORGANISM: Homo sapiens

<400> SEQUENCE: 71
gtgcatgagg aaggccttc                    19

<210> SEQ ID NO 72
<211> LENGTH: 19
<212> TYPE: DNA
<213> ORGANISM: Homo sapiens

<400> SEQUENCE: 72
ctggaccacc tggaacacc                    19

<210> SEQ ID NO 73
<211> LENGTH: 19
<212> TYPE: DNA
<213> ORGANISM: Homo sapiens

<400> SEQUENCE: 73
caccaacgtg ggcatcatc                    19

<210> SEQ ID NO 74
<211> LENGTH: 19
<212> TYPE: DNA

<213> ORGANISM: Homo sapiens

<400> SEQUENCE: 74
cgtgggcatc atcaacgaa        19

<210> SEQ ID NO 75
<211> LENGTH: 19
<212> TYPE: DNA
<213> ORGANISM: Homo sapiens

<400> SEQUENCE: 75
cgaagacccg ggcaactgt        19

<210> SEQ ID NO 76
<211> LENGTH: 19
<212> TYPE: DNA
<213> ORGANISM: Homo sapiens

<400> SEQUENCE: 76
gcagagtttc aggcagaca        19

<210> SEQ ID NO 77
<211> LENGTH: 19
<212> TYPE: DNA
<213> ORGANISM: Homo sapiens

<400> SEQUENCE: 77
gaactttgcc ctggtcccc        19

<210> SEQ ID NO 78
<211> LENGTH: 19
<212> TYPE: DNA
<213> ORGANISM: Homo sapiens

<400> SEQUENCE: 78
ctttgccctg gtcccccctt        19

<210> SEQ ID NO 79
<211> LENGTH: 19
<212> TYPE: DNA
<213> ORGANISM: Homo sapiens

<400> SEQUENCE: 79
gagaggcaag tgctcgaga        19

<210> SEQ ID NO 80
<211> LENGTH: 19
<212> TYPE: DNA
<213> ORGANISM: Homo sapiens

<400> SEQUENCE: 80
gtgctcgaga taggcagtc        19

<210> SEQ ID NO 81
<211> LENGTH: 19
<212> TYPE: DNA
<213> ORGANISM: Homo sapiens

<400> SEQUENCE: 81
gtttatctgc gacagtttt        19

<210> SEQ ID NO 82
<211> LENGTH: 19
<212> TYPE: RNA

```
<213> ORGANISM: Homo sapiens
<220> FEATURE:
<221> NAME/KEY: misc_feature
<223> OTHER INFORMATION: rna sequence complementary to seq 1

<400> SEQUENCE: 82
cuuuaccucg ucgugucug                                                    19

<210> SEQ ID NO 83
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 2

<400> SEQUENCE: 83
uaccucgucg ugucugaac                                                    19

<210> SEQ ID NO 84
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 3

<400> SEQUENCE: 84
accucgucgu gucugaacc                                                    19

<210> SEQ ID NO 85
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 4

<400> SEQUENCE: 85
uuccugugga cgggucugg                                                    19

<210> SEQ ID NO 86
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 5

<400> SEQUENCE: 86
cugggagucc gagauacua                                                    19

<210> SEQ ID NO 87
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 6

<400> SEQUENCE: 87
cggcaacgag ucuuauuga                                                    19

<210> SEQ ID NO 88
<211> LENGTH: 19
<212> TYPE: RNA
<213> ORGANISM: Homo sapiens
<220> FEATURE:
```

<221> NAME/KEY: misc_feature
<223> OTHER INFORMATION: rna sequence complementary to seq 7

<400> SEQUENCE: 88
auugacgguc cuagaccuc                                                19

<210> SEQ ID NO 89
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 8

<400> SEQUENCE: 89
gacgguccua gaccucucg                                                19

<210> SEQ ID NO 90
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 9

<400> SEQUENCE: 90
cucguucuuc guggagugu                                                19

<210> SEQ ID NO 91
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 10

<400> SEQUENCE: 91
cuucguggag ugucuguug                                                19

<210> SEQ ID NO 92
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complmentary to seq 11

<400> SEQUENCE: 92
cguggagugu cuguugcuc                                                19

<210> SEQ ID NO 93
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complmentary to seq 12

<400> SEQUENCE: 93
gcucaaguuu cuggacuc                                                 19

<210> SEQ ID NO 94
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 13

```
<400> SEQUENCE: 94
ucugggacuc ugucccuuc                                            19

<210> SEQ ID NO 95
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 14

<400> SEQUENCE: 95
cugggacucu gucccuucu                                            19

<210> SEQ ID NO 96
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 15

<400> SEQUENCE: 96
cuggacagac gacuuucgg                                            19

<210> SEQ ID NO 97
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 16

<400> SEQUENCE: 97
ucgguacgag uuggacgua                                            19

<210> SEQ ID NO 98
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 17

<400> SEQUENCE: 98
cgguacgagu uggacguac                                            19

<210> SEQ ID NO 99
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 18

<400> SEQUENCE: 99
ggacguacug ccugucuug                                            19

<210> SEQ ID NO 100
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 19

<400> SEQUENCE: 100
```
ugccugucgg acuuccucg                                                    19

<210> SEQ ID NO 101
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 20

<400> SEQUENCE: 101
gccugucgga cuuccucga                                                    19

<210> SEQ ID NO 102
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 21

<400> SEQUENCE: 102
ccucgaacag uugcggucg                                                    19

<210> SEQ ID NO 103
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to sequence 22

<400> SEQUENCE: 103 cuuugguuu cccgccgga                                                     19

<210> SEQ ID NO 104
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 23

<400> SEQUENCE: 104
uugguuuccc gccggaccu                                                    19

<210> SEQ ID NO 105
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 24

<400> SEQUENCE: 105
ugguuucccg ccggaccua                                                    19

<210> SEQ ID NO 106
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 25

<400> SEQUENCE: 106
gguuucccgc cggaccuaa                                                    19

```
<210> SEQ ID NO 107
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 26

<400> SEQUENCE: 107
ucccgccgga ccuaagaug                                                19

<210> SEQ ID NO 108
<211> LENGTH: 19
<212> TYPE: RNA
<213> ORGANISM: Homo sapiens
<220> FEATURE:
<221> NAME/KEY: misc_feature
<223> OTHER INFORMATION: sequence complementary to seq 27

<400> SEQUENCE: 108
cccgccggac cuaagauga                                                19

<210> SEQ ID NO 109
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 28

<400> SEQUENCE: 109
ggucgacccg uagcacuuc                                                19

<210> SEQ ID NO 110
<211> LENGTH: 19
<212> TYPE: RNA
<213> ORGANISM: Homo sapiens
<220> FEATURE:
<221> NAME/KEY: misc_feature
<223> OTHER INFORMATION: rna sequecne complementary to seq 29

<400> SEQUENCE: 110
caaggacgac gucuugagg                                                19

<210> SEQ ID NO 111
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 30

<400> SEQUENCE: 111
gugccggcug uugugcuuc                                                19

<210> SEQ ID NO 112
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 31

<400> SEQUENCE: 112
gugcuucaaa cacugcucg                                                19
```

<210> SEQ ID NO 113
<211> LENGTH: 19
<212> TYPE: RNA
<213> ORGANISM: Homo sapiens
<220> FEATURE:
<221> NAME/KEY: misc_feature
<223> OTHER INFORMATION: rna sequence comlementary to seq 32

<400> SEQUENCE: 113
caaacacugc ucguacaug                                                    19

<210> SEQ ID NO 114
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 33

<400> SEQUENCE: 114
acucuaagac uaggacccc                                                    19

<210> SEQ ID NO 115
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 34

<400> SEQUENCE: 115
ugacgugggc ugcgacuuc                                                    19

<210> SEQ ID NO 116
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 35

<400> SEQUENCE: 116
cgaccuccuc gagugguug                                                    19

<210> SEQ ID NO 117
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 36

<400> SEQUENCE: 117
guucuucccu uacugcggc                                                    19

<210> SEQ ID NO 118
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 37

<400> SEQUENCE: 118
cuucccuuac ugcggcgac                                                    19

<210> SEQ ID NO 119
<211> LENGTH: 19

```
<212> TYPE: RNA
<213> ORGANISM: Homo sapiens
<220> FEATURE:
<221> NAME/KEY: misc_feature
<223> OTHER INFORMATION: rna sequence complementary to seq 38

<400> SEQUENCE: 119
cuagccccag aaccggaua                                                    19

<210> SEQ ID NO 120
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 39

<400> SEQUENCE: 120
caaguggcuc acccggaug                                                    19

<210> SEQ ID NO 121
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 40

<400> SEQUENCE: 121
cuugagccac gaccuccac                                                    19

<210> SEQ ID NO 122
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 41

<400> SEQUENCE: 122
gagccacgac cuccacuag                                                    19

<210> SEQ ID NO 123
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 42

<400> SEQUENCE: 123
agcggugcug uacgagaac                                                    19

<210> SEQ ID NO 124
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 43

<400> SEQUENCE: 124
ggcugaggac guccuguuc                                                    19

<210> SEQ ID NO 125
<211> LENGTH: 19
<212> TYPE: RNA
<213> ORGANISM: Homo sapiens
```

```
<220> FEATURE:
<221> NAME/KEY: misc_feature
<223> OTHER INFORMATION: rna complementary to seq 44

<400> SEQUENCE: 125
cacccugucu aagcaguuc                                                      19

<210> SEQ ID NO 126
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 45

<400> SEQUENCE: 126
cgcguagaag augaaguug                                                      19

<210> SEQ ID NO 127
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 46

<400> SEQUENCE: 127
gaaggaccag augacggac                                                      19

<210> SEQ ID NO 128
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 47

<400> SEQUENCE: 128
cuaccuuuuu uaaccucug                                                      19

<210> SEQ ID NO 129
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 48

<400> SEQUENCE: 129
uuuaaccucu gauaaaggc                                                      19

<210> SEQ ID NO 130
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 49

<400> SEQUENCE: 130
uuaaccucug auaaaggcu                                                      19

<210> SEQ ID NO 131
<211> LENGTH: 19
<212> TYPE: RNA
<213> ORGANISM: Homo sapiens
<220> FEATURE:
<221> NAME/KEY: misc_feature
```

<223> OTHER INFORMATION: rna complementary to seq 50

<400> SEQUENCE: 131
uaaccucuga uaaaggcuc                                                    19

<210> SEQ ID NO 132
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 51

<400> SEQUENCE: 132
aaccucugau aaaggcuca                                                    19

<210> SEQ ID NO 133
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 52

<400> SEQUENCE: 133
cugggacaaa caccugucg                                                    19

<210> SEQ ID NO 134
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 53

<400> SEQUENCE: 134
ccucauacac cgaagguac                                                    19

<210> SEQ ID NO 135
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 54

<400> SEQUENCE: 135
guacgagaug augugggcg                                                    19

<210> SEQ ID NO 136
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 55

<400> SEQUENCE: 136
cuacuaggac ucucuggac                                                    19

<210> SEQ ID NO 137
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 56

```
<400> SEQUENCE: 137
cugcccuucu uacugaggg                                                  19

<210> SEQ ID NO 138
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 57

<400> SEQUENCE: 138
cuuacugagg gacggcaga                                                  19

<210> SEQ ID NO 139
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 58

<400> SEQUENCE: 139
acugagggac ggcagacuc                                                  19

<210> SEQ ID NO 140
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 59

<400> SEQUENCE: 140
gucggacaug agguggacg                                                  19

<210> SEQ ID NO 141
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 60

<400> SEQUENCE: 141
caagugguag ccguacccg                                                  19

<210> SEQ ID NO 142
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 61

<400> SEQUENCE: 142
gauacugaag uuccgacag                                                  19

<210> SEQ ID NO 143
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 62

<400> SEQUENCE: 143
```
ccgacagaag uaguaggac                                               19

<210> SEQ ID NO 144
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 63

<400> SEQUENCE: 144
aagaguggau guaggagga                                               19

<210> SEQ ID NO 145
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 64

<400> SEQUENCE: 145
guacgaguag cgggaguac                                               19

<210> SEQ ID NO 146
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 65

<400> SEQUENCE: 146
guucuagcgu guccucucg                                               19

<210> SEQ ID NO 147
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 66

<400> SEQUENCE: 147
cuagcguguc cucucguuc                                               19

<210> SEQ ID NO 148
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 67

<400> SEQUENCE: 148
cuuguagacc uucgacguc                                               19

<210> SEQ ID NO 149
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 68

<400> SEQUENCE: 149
guagaccuuc gacgucucu                                               19

<210> SEQ ID NO 150
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 69

<400> SEQUENCE: 150
cgacgucucu cgguagugg                                                19

<210> SEQ ID NO 151
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 70

<400> SEQUENCE: 151
cucgaaggaa uucacguac                                                19

<210> SEQ ID NO 152
<211> LENGTH: 19
<212> TYPE: RNA
<213> ORGANISM: Homo sapiens
<220> FEATURE:
<221> NAME/KEY: misc_feature
<223> OTHER INFORMATION: rna sequence complementary to seq 71

<400> SEQUENCE: 152
cacguacucc uuccggaag                                                19

<210> SEQ ID NO 153
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 72

<400> SEQUENCE: 153
gaccuggugg accuugugg                                                19

<210> SEQ ID NO 154
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 73

<400> SEQUENCE: 154
gugguugcac ccguaguag                                                19

<210> SEQ ID NO 155
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 74

<400> SEQUENCE: 155
gcacccguag uaguugcuu                                                19

<210> SEQ ID NO 156

```
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 75

<400> SEQUENCE: 156 gcuucgggc ccguugaca                                                19

<210> SEQ ID NO 157
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 76

<400> SEQUENCE: 157
cgucucaaag uccgucugu                                               19

<210> SEQ ID NO 158
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 77

<400> SEQUENCE: 158
cuugaaacgg gaccagggg                                               19

<210> SEQ ID NO 159
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 78

<400> SEQUENCE: 159
gaaacgggac caggggggaa                                              19

<210> SEQ ID NO 160
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 79

<400> SEQUENCE: 160
cucuccguuc acgagcucu                                               19

<210> SEQ ID NO 161
<211> LENGTH: 19
<212> TYPE: RNA
<213> ORGANISM: Homo sapiens
<220> FEATURE:
<221> NAME/KEY: misc_feature
<223> OTHER INFORMATION: rna complementary to seq 80

<400> SEQUENCE: 161
cacgagcucu auccgucag                                               19

<210> SEQ ID NO 162
<211> LENGTH: 19
<212> TYPE: RNA
```

-continued

```
<213> ORGANISM: Homo sapiens
<220> FEATURE:
<221> NAME/KEY: misc_feature
<223> OTHER INFORMATION: rna complementary to seq 81

<400> SEQUENCE: 162
caaauagacg cugucaaaa                                                        19
```

MODULATION OF TRPV EXPRESSION LEVELS

FIELD OF THE INVENTION

The present invention relates to methods and compositions for the treatment and/or the prevention of conditions related to high levels of expression and/or activity of the transient receptor potential vanilloid-1 (TRPV1). Amongst others, eye conditions such as discomfort and altered sensitivity of the cornea following refractive surgery, use of contact lenses, dry eyes and diabetic retinopathy, are to be mitigated.

Methods and compositions for the treatment and/or the prevention of hair follicle and skin abnormal conditions mediated by high levels of expression and/or activity of TRPV1, such as alopecia, are also provided. In preferred embodiments, the invention relates to the use of RNAi technology to downregulate the expression of TRPV1.

BACKGROUND OF THE INVENTION

RNA interference refers to the process of sequence-specific post-transcriptional gene silencing mediated by short interfering RNAs (siRNA). After the discovery of the phenomenon in plants in the early 1990s, Andy Fire and Craig Mello demonstrated that double-stranded RNA (dsRNA) specifically and selectively inhibited gene expression in an extremely efficient manner in *Caenorhabditis elegans* (Fire et al., 1998, Potent and specific genetic interference by double stranded RNA in *Caenorhabditis elegans*. Nature, 391:806). The sequence of the first strand (sense RNA) coincided with that of the corresponding region of the target messenger RNA (mRNA). The second strand (antisense RNA) was complementary to the mRNA. The resulting dsRNA turned out to be several orders of magnitude more efficient than the corresponding single-stranded RNA molecules (in particular, antisense RNA).

The process of RNAi begins when the enzyme, DICER, encounters dsRNA and chops it into pieces called small-interfering RNAs (siRNA). This protein belongs to the RNase III nuclease family. A complex of proteins gathers up these RNA remains and uses their code as a guide to search out and destroy any RNAs in the cell with a matching sequence, such as target mRNA (see Bosher & Labouesse, 2000, RNA interference: genetic wand and genetic watchdog. Nat Cell Biol, 2000, 2 (2):E31, and Akashi et al., 2001, Suppression of gene expression by RNA interference in cultured plant cells. Antisense Nucleic Acid Drug Dev, 11 (6):359).

In attempting to utilize RNAi for gene knockdown, it was recognized that mammalian cells have developed various protective mechanisms against viral infections that could impede the use of this approach Indeed, the presence of extremely low levels of viral dsRNA triggers an interferon response, resulting in a global non-specific suppression of translation, which in turn triggers apoptosis (Williams, 1997, Role of the double-stranded RNA-activated protein kinase (PKR) in cell regulation. Biochem Soc Trans, 25 (2):509; Gil & Esteban, 2000, Induction of apoptosis by the dsRNA-dependent protein kinase (PKR): mechanism of action. Apoptosis, 5 (2): 107-14).

In 2000 dsRNA was reported to specifically inhibit 3 genes in the mouse oocyte and early embryo. Translational arrest, and thus a PKR response, was not observed as the embryos continued to develop (Wianny & Zernicka-Goetz, 2000, Specific interference with gene function by double-stranded RNA in early mouse development. Nat Cell Biol, 2 (2):70). Research at Ribopharma AG (Kulmbach, Germany) demonstrated the functionality of RNAi in mammalian cells, using short (20-24 base pairs) dsRNA to switch off genes in human cells without initiating the acute-phase response. Similar experiments carried out by other research groups confirmed these results. (Elbashir et al., 2001, RNA interference is mediated by 21- and 22-nucleotide RNAs. Genes Dev, 15 (2):188; Caplen et al., 2001, Specific inhibition of gene expression by small double stranded RNAs in invertebrate and vertebrate systems. Proc. Natl. Acad. Sci. USA, 98: 9742). Tested in a variety of normal and cancer human and mouse cell lines, it was determined that short hairpin RNAs (shRNA) can silence genes as efficiently as their siRNA counterparts (Paddison et al, 2002, Short hairpin RNAs (shRNAs) induce sequence-specific silencing in mammalian cells. Genes Dev, 16 (8): 948). Recently, another group of small RNAs (21-25 base pairs) was shown to mediate downregulation of gene expression. These RNAs, small temporally regulated RNAs (stRNA), regulate timing of gene expression during development in *Caenorhabditis elegans* (for review see Banerjee & Slack, Control of developmental timing by small temporal RNAs: a paradigm for RNA-mediated regulation of gene expression. Bioessays, 2002, 24 (2):119-29 and Grosshans & Slack, 2002, Micro-RNAs: small is plentiful. J Cell Biol, 156 (1):17).

Scientists have used RNAi in several systems, including *Caenorhabditis elegans, Drosophila*, trypanosomes, and other invertebrates. Several groups have recently presented the specific suppression of protein biosynthesis in different mammalian cell lines (specifically in HeLa cells) demonstrating that RNAi is a broadly applicable method for gene silencing in vitro. Based on these results, RNAi has rapidly become a well recognized tool for validating (identifying and assigning) gene function. RNAi employing short dsRNA oligonucleotides will yield an understanding of the function of genes that are only partially sequenced.

The transient receptor potential vanilloid-1 (TRPV1), also called Vanilloid receptor 1 (VR-1), is a capsaicin-responsive ligand-gated cation channel, that was first discovered in 1997 (Caterina et al. The capsaicin receptor: a heat-activated ion channel in the pain pathway. Nature. 1997 Oct. 23; 389 (6653):816-24). TRPV1 is mainly expressed on sensory neurons and serves as a molecular detector for heat, capsaicin, protons, and endovanilloids (Caterina M J & Julius D. The vanilloid receptor: a molecular gateway to the pain pathway. Annu Rev Neurosci., 2001; 24:487-517; Montell et al. Short hairpin RNAs (shRNAs) induce sequence-specific silencing in mammalian cells. Genes Dev., 2002, 16 (8):948-58; Baumann T K & Martenson M E. Extracellular protons both increase the activity and reduce the conductance of capsaicin-gated channels. J Neurosci. 2000; 20:RC80).

When TRPV1 is activated by agonists such as capsaicin and other factors such as heat, acidosis, lipoxygenase products or anandamide, calcium enters the cell and pain signals are initiated. Activation of the channel induces neuropeptide release from central and peripheral sensory nerve terminals, resulting in the sensation of pain, neurogenic inflammation, and sometimes, in smooth muscle contraction and cough. Recent evidence suggests a role of TRPV1 in pain, cough, asthma and urinary incontinence (Jia et al., TRPV1 receptor: a target for the treatment of pain, cough, airway disease and urinary incontinence. Drug News Perspect. 2005 April; 18 (3):165-71).

Due to the fact that both the sensitivity and the density of expression of TRPV1 are enhanced during inflammatory conditions (Di Marzo et al., Endovanilloid signaling in pain. Curr Opin Neurobiol. 2002 August; 12 (4):372-9), downregulation of TRPV1 expression and/or activity is a promising therapeutic strategy for novel analgesic drugs. As a matter of fact, intraperitoneal administration of selective TRPV1 blockers into mice proved to attenuate chemical and thermal nociception and hyperalgesia (Garcia-Martinez et al., Attenuation of thermal nociception and hyperalgesia by VR1 blockers. Proc Natl Acad Sci USA. 2002 Feb. 19; 99 (4):2374-9).

TRPV1 channel function is upregulated by several endogenous mediators present in inflammatory conditions, which decrease the threshold for activation of the channel. Thus, it has recently been demonstrated that acute pain-related behaviour evoked by elevated ionic strength is abolished in TRPV1-null mice and inhibited by iodoresiniferatoxin, a potent TRPV1 antagonist (Ahern et al., Extracellular cations sensitize and gate capsaicin receptor TRPV1 modulating pain signaling. J Neurosci. 2005 May 25; 25 (21):5109-16). Further, Prostaglandin $E_2$ ($PGE_2$) and Prostaglandin $I_2$ ($PGI_2$) have proven to increase or sensitize TRPV1 responses through their respective receptors $EP_1$ or IP (Moriyama et al., Sensitization of TRPV1 by EP1 and IP reveals peripheral nociceptive mechanism of prostaglandins. Mol Pain. 2005 Jan 17; 1 (1):3), suggesting for the first time that sensitisation of TRPV1 activity through $EP_1$ or IP activation might be one important mechanism underlying the peripheral nociceptive actions of $PGE_2$ or $PGI_2$. WO 2004/042046 shows that siRNA targeted against VR1 can be used in the treatment of chronic pain, sensitivity disfunctions linked to the VR1 receptor and VR associated inflammation, tumours urinary incontinence and pruritus.

Polymodal nociceptors are the most abundant nociceptor type found in the cornea. There exists pharmacological evidence that these receptor fibers express the TRPV1 receptor because they respond to capsaicin, heat and acid. Moreover, high doses of capsaicin inactivate the activation of corneal polymodal nociceptors to heat and acid whereas mechanical responsiveness remains unaffected. This suggests that TRPV1 receptors present in corneal polymodal nerve endings were selectively inactivated. Therefore, it is likely that an important part of the acute nociceptive response to corneal injury and the sustained pain sensations that accompany inflammatory and irritative processes in this tissue are mediated by TRPV1 activation.

Recent evidence also demonstrates that both insulin and IGF-I enhance TRPV1-mediated membrane currents in heterologous expression systems and cultured dorsal root ganglion neurons (Van Buren et al., Sensitization and translocation of TRPV1 by insulin and IGF-I. Mol Pain. 2005 Apr. 27; 1 (1):17). Enhancement of membrane currents results from both increased sensitivity of the receptor and translocation of TRPV1 from cytosol to plasma membrane. An increase of IGF-1 has been found in the serum (Merimee et al., Insulin-like growth factors. Studies in diabetics with and without retinopathy. N. Engl. J. Med., 1983; 309:527-530; Grant et al., Insulin-like growth factors in vitreous. Studies in control and diabetic subjects with neovascularization. Diabetes, 1986; 35:416-420) and the vitreous body and intraocular fluid (Grant et al., 1986; Inokuchi et al., Vitreous levels of insulin-like growth factor-I in patients with proliferative diabetic retinopathy. Curr. Eye Res., 2001; 23:368-371) of patients with diabetic retinopathy. Further, vitreous IGF-I levels correlate with the presence and severity of ischemia-associated diabetic retinal neovascularization (Meyer-Schwickerath et al., Vitreous levels of the insulin-like growth factors I and II, and the insulin-like growth factor binding proteins 2 and 3, increase in neovascular eye disease. Studies in nondiabetic and diabetic subjects. J Clin Invest., 1993; 92 (6):2620-5). However, the source of increased ocular IGF-1 in retinopathy is controversial, and the relative contribution of either endogenous IGF-1 or serum IGF-1 is unknown (Ruberte et al., Increased ocular levels of IGF-1 in transgenic mice lead to diabetes-like eye disease. J Clin Invest. 2004 April; 113 (8): 1149-57). Modulation of TRPV1 levels could aid in the control of diabetic retinopathy mediated by IGF-I.

Although originally described on sensory neurons, TRPV1 has now been detected in several human skin cell populations and epithelial compartments of the human hair follicle (HF), mainly the outer root sheath (ORS) and hair matrix (Bodo et al., A hot new twist to hair biology: involvement of vanilloid receptor-1 (VR1/TRPV1) signaling in human hair growth control. Am J Pathol. 2005 April; 166 (4):985-98). Stimulation of TRPV1 in organ culture and cultured human ORS keratinocytes inhibits proliferation, induces apoptosis, elevates intracellular calcium concentration, up-regulates known endogenous hair growth inhibitors, and down-regulates known hair growth promoters, thus supporting TRPV1 as a significant novel player in human hair growth control (Bodo et al., 2005).

The above-mentioned evidence points to inhibition of TRPV1 as an efficient treatment for eye conditions that mediate with an excess of expression and/or activity of TRPV1, such as discomfort and altered sensitivity of the cornea following refractive surgery, use of contact lenses and dry eyes. The functional relationship between TRPV1 and IGF-I highlights the importance of downregulation of TRPV1 for the treatment of diabetic retinopathy mediated by high levels of IGF-I. The role played by TRPV1 in human hair follicle growth and keratinocytes targets TRPV1 as a good candidate to be inhibited for the treatment of hair follicle and skin abnormal conditions such as alopecia.

SUMMARY OF THE INVENTION

In the present invention we describe a method for the treatment and/or prevention of conditions related to high levels of TRPV1, comprising eye and hair follicle abnormal conditions. The method is based on the downregulation of expression of one or more splice forms of the TRPV1 gene. Inhibition (downregulation) may be effected by the use of double stranded nucleic acid moieties, named siNA or small interfering NA that are directed at interfering with the mRNA expression of either one or more splicing forms of the TRPV1 gene. The siNA are preferably siRNA, although modified nucleic acids or similar chemically synthesised entities are also included within the scope of the invention.

The TRPV1 receptor, like other membrane proteins and channels is manufactured inside the cell and transported to the periphery by centrifugal axonal transport. Nevertheless, the possibility exists that TRPV1 is also synthetized at the sensory nerve terminals, being inserted locally into the membrane of the transducing portion of the ending. Therefore, without wishing to be bound by theory, it is suggested that blockade of the local synthesis of TRPV1 through topical administration of siNA directed to specifically silence the gene in charge of TRPV1 expression might lead to a partial or complete inactivation of polymodal nociceptor fibers of the cornea to chemical stimuli by exogenous or endogenous stimuli and to a reduction or elimination of their impulse activity associated to injury and inflammation.

In a first aspect of the present invention relates to the use of siNA in the preparation of a medicament for use in a method of treatment of an eye and/or hair follicle abnormal condition characterised by increased expression and/or activity of TRPV1.

A second aspect of the present invention relates to a siNA compound targeted to TRVP1.

Another aspect of the present invention relates to a pharmaceutical composition comprising a siNA compound targeted to TRPV1.

A further aspect of the present invention provide method of treatment of a disease characterised by increased expression and/or activity of TRPV1, comprising administering siNA to inhibit expression of TRPV1 gene in a patient, wherein the disease condition is selected from the group comprising an abnormal eye condition, such as altered sensitivity of the cornea following refractive surgery, use of contact lenses, dry eyes, diabetic retinopathy, and other eye pathologies, as well as a hair follicle abnormal condition such as alopecia.

DESCRIPTION OF THE DRAWINGS

FIG. 1A-1B show short DNA fragments of the target gene sequence chosen as preferred target sequences of the siNA of the invention.

FIG. 2A-2D show preferred siNA molecules of the invention.

DETAILED DESCRIPTION OF THE INVENTION

Figure 3:
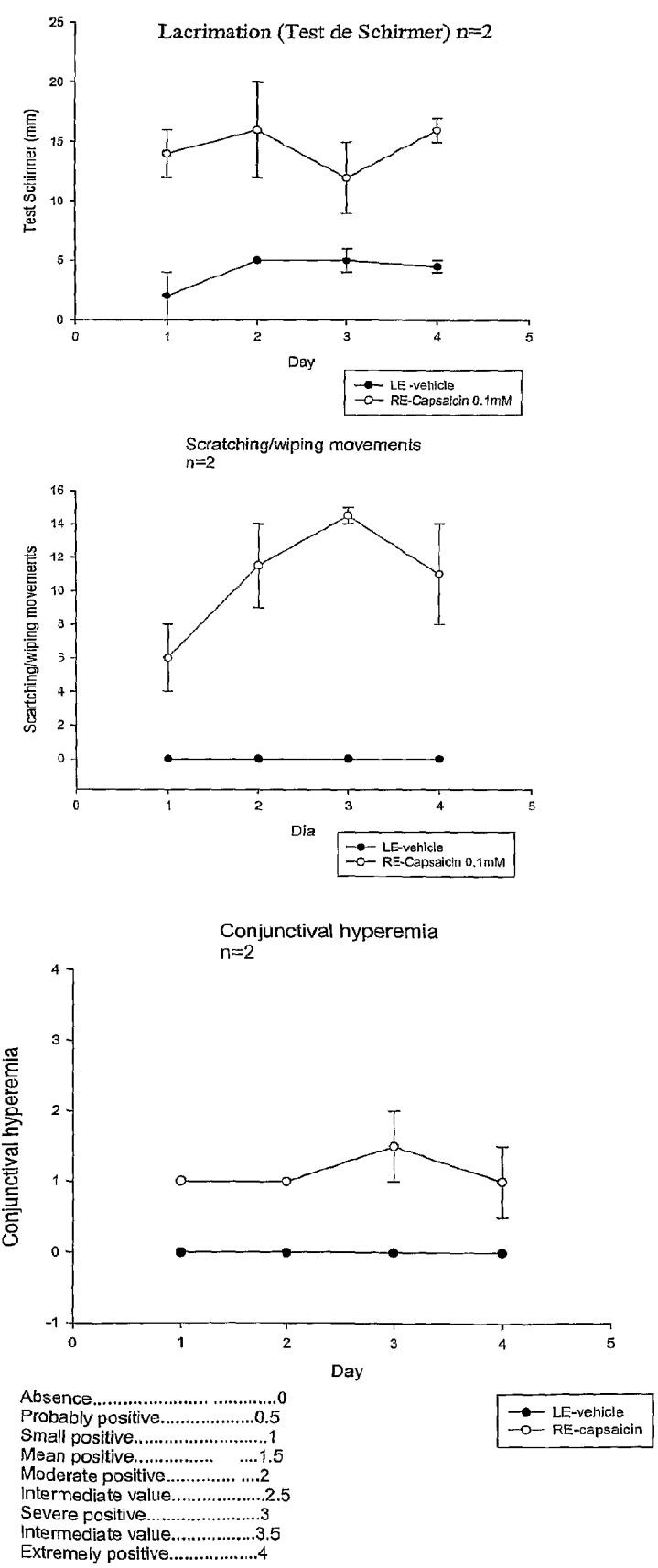
FIG. 3. Effect of topical application of a 10 μL drop of 0.1 mM capsaicin solution in the right eye and of 10 μL of sterile isotonic saline in the left eye of guinea pigs. Scratching and wiping movements (A), Tearing (B) and Conjunctival hyperemia (C) were analysed.

In a first aspect, the invention relates to the use of siNA in the preparation of a medicament for use in a method of treatment of an eye and/or hair follicle abnormal condition characterised by increased expression and/or activity of TRPV1. The method may comprise inhibiting the expression of TRPV1 in a patient. The term inhibition is used to indicate a decrease or downregulation of expression or activity. Preferably, the eye condition is selected from the group comprising discomfort and altered sensitivity of the cornea following refractive surgery, use of contact lenses, dry eyes, diabetic retinopathy, and other eye pathologies. Also preferably, the abnormal hair follicle condition is alopecia.

A gene is "targeted" by a siNA according to the present invention when, for example, the siNA molecule selectively decreases or inhibits the expression of the gene. The phrase "selectively decrease or inhibit" as used herein encompasses siNAs that effects expression of one gene. Alternatively, a siNA targets a gene when the siNA hybridizes under stringent conditions to the gene transcript.

In one embodiment, siNA according to the invention is siRNA.

Four transcript variants corresponding to TRPV1 have been identified.

GenBank Accession Numbers corresponding to the four TRPV1 transcripts produced by alternative splicing are displayed in FIG. 1. Preferably, the siNA is targeted to a splice form of TRPV1 selected from the group having GenBank Accession Numbers NM_080704, NM_018727, NM_080706, NM_080705.

Selected oligonucleotide sequences against which RNAi is directed according to the first aspect of the invention are shown in FIGS. 1A-1B. Displayed sequences are the DNA sequences targeted by the siNA. Therefore, the invention makes use of NA duplexes with sequences complementary to the indicated DNA sequences. Therefore, in accordance with the first aspect of the invention, siNA is targeted to a sequence selected from SEQ ID NO 1 to SEQ ID NO 81 or to a sequence comprising a sequence selected from SEQ ID NO 1 to SEQ ID NO 81. Thus, the siNA is complementary to a sequence selected from SEQ ID NO 1 to SEQ ID NO 81 or to a sequence comprising a sequences selected from SEQ ID NO 1 to SEQ ID NO 81.

According to the invention, a plurality of siNA species may be used. In one embodiment, the plurality of siNA species may be targeted to the same mRNA species, in another embodiment, it may be targeted to different species.

The sequences displayed in FIGS. 1A-1B are not limiting. According to the invention, target DNA need not necessarily be preceded by AA or CA. Further, target DNA could be constituted by sequences included in FIGS. 1A-1B flanked by any contiguous sequence.

In another preferred embodiment, the invention relates to a siNA compound targeted to TRVP1 comprising a nucleotide sequence complementary to a nucleotide sequence selected from SEQ ID NO 1 to 44 or SEQ ID NO 46 to 81 as shown in FIGS. 1A-1B. In one embodiment, the preferred SEQ is SEQ ID NO 65.

In a further embodiment, the invention relates to a siNA compound targeted to TRVP1 comprising a nucleotide sequence complementary to a nucleotide sequence selected from SEQ ID NO 1 to 44 or SEQ ID NO 46 to 81 for use in the treatment of a disease characterized by increased expression and/or activity of TRPV1, the siNA comprising a nucleotide sequence complementary to a nucleotide sequence selected from SEQ ID NO 1 to 44 or SEQ ID NO 46 to 81.

In a further aspect, the invention relates to a pharmaceutical composition comprising a nucleotide sequence complementary to a nucleotide sequence selected from SEQ ID NO 1 to 44 or SEQ ID NO 46 to 81.

In one embodiment, siNA molecules of the present invention comprise nucleotide sequences selected from the group of SEQ ID NO 82 to 162. For example, siNA molecules of the present invention comprise nucleotide sequences selected from the group of SEQ ID NO 82 to 122 or 123 to 162.

In preferred embodiments, siNA molecules comprise overhanging nucleotides.

The invention also relates to a method for inhibiting expression and/or activity of TRPV1 ex vivo in cells or tissue comprising treating said cells or tissue with the compound comprising a nucleotide sequence complementary to a nucleotide sequence selected from SEQ ID NO 1 to 44 or SEQ ID NO 46 to 81 so that TRVP1 expression is inhibited.

In a final aspect, the invention relates to a method of treatment of a disease characterised by increased expression and/or or activity of TRPV1, comprising administering siNA to inhibit expression of TRPV1 gene in a patient wherein the disease condition is selected from the group comprising an abnormal eye condition, such as altered sensitivity of the cornea following refractive surgery, use of contact lenses, dry eyes, diabetic retinopathy, and other eye pathologies, as well as a hair follicle abnormal condition such as alopecia.

The terms "treating" or "treatment" as used herein describe the management or care of a patient for the purposes of combating disease, and includes the administration of the active agent to asymptomatic individuals, for example to prevent the onset of the symptoms or complications, i.e. prophylaxis.

The invention also relates to a pharmaceutical composition comprising the siNA compound as described herein.

Design of siNAs.

A short fragment of the target gene sequence (e.g., 19-40 nucleotides in length) is chosen as the target sequence of the siNA of the invention. In one embodiment, the siNA is a siRNA. In such embodiments, the short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, and 5) a sequence from the target gene mRNA that is unique to the target gene. The sequence fragment from the target gene mRNA may meet one or more of the criteria identified supra. In embodiments where a fragment of the target gene mRNA meets less than all of the criteria identified supra, the native sequence may be altered such that the siRNA conforms with more of the criteria than does the fragment of the target gene mRNA. In preferred embodiments, the siRNA has a G/C/content below 60% and/or lacks repetitive sequences.

Practically, the selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides (typically 21 bp long, although other lengths are also possible) that are typically made by chemical synthesis.

In addition to siNA which is complementary to the mRNA target region, degenerate siNA sequences may be used according to the invention to target homologous regions. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology.

In preferred embodiments, siNA molecules of the invention target a sequence selected from SEQ ID NOS: 1-81 (FIGS. 1A-1B).

Preferred siNA molecules of the invention are double stranded. In one embodiment, double stranded siNA molecules comprise blunt ends. In another embodiment, double stranded siNA molecules comprise overhanging nucleotides (e.g., 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g., other than phosphodiester bond).

In preferred embodiments, siNA molecules of the invention comprise nucleotide sequences selected from SEQ ID NOS: 82-162 (FIGS. 2A-2D). In another preferred embodiment, dsRNA compositions of the invention are any of SEQ ID NOS: 82-162. The invention also encompasses siNAs that are 40 nucleotides or less and comprise a nucleotide sequence of any of SEQ ID NOS: 82-162 as well as dsRNA compositions that are 40 nucleotides or less and comprise a nucleotide sequence of any of SEQ ID NOS: 82-162 hybridized to its compliment. In one embodiment, the siNA is 21-30 nucleotides and comprises any one of SEQ ID NOS: 82-162.

Synthesis of siNAs.

siNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany), Ambion (USA) and Invitrogen (Scotland). Alternatively, siNA molecules of the invention can be expressed in cells by transfecting the cells with vectors containing the reverse compliment siNA sequence under the control of a promoter. Once expressed, the siNA can be isolated from the cell using techniques well known in the art.

In embodiments where the siRNA is a dsRNA, an annealing step is necessary if single-stranded RNA molecules are obtained. Briefly, combine 30 µl of each RNA oligo 50 µM solution in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA); the two strands of the siRNA molecule may be connected by a linker region (e.g., a nucleotide linker or a non-nucleotide linker).

Chemical Modification of siNAs.

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications WO03/070744 and WO2005/045037 for an overview of types of modifications). In one embodiment, modifications can be used to provide improved resistance to degradation or improved uptake. Examples of such modifications include phosphorothioate internucleotide linkages, 2'-O-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication WO2004/029212).

In another embodiment, modifications can be used to increased or decreased affinity for the complementary nucleotides in the target mRNA and/or in the complementary siNA strand (see generally International Publication WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides (see generally Elbashir et al., 2001, Genes Dev, 15:188).

Formulations and Routes of Administration.

The siNA molecules of the invention and formulations or compositions thereof may be administered directly or topically (e. g., locally) to the organ of interest (for example, eye, skin, etc) as is generally known in the art. For example, administration may be intrarticular or intravenous. In a preferred embodiment, administration may be ocular, for example by means of eye drops.

For example, a siNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

A siNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e. g., fatty acids, fatty acid esters, fatty alcohols and amino acids), and hydrophilic polymers (e. g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

Generally, an amount between 0.1 mg/kg and 100 mg/kg body weight/day of active ingredients is administered.

The formulations of the invention can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations.

These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agents. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain siNA molecules of the invention can be expressed within cells from eukaryotic promoters. Recombinant vectors capable of expressing the siNA molecules can be delivered and persist in target cells. Alternatively, vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell.

Experimental Procedure

SiNA Synthesis

An annealing step is necessary when working with single-stranded RNA molecules. It is critical that all handling steps be conducted under sterile, Rnase free conditions. To anneal the RNAs, the oligos must first be quantified by UV absorption at 260 nanometres (nm). The following protocol based on Elbashir et al. (2001) is then used for annealing:

Separately aliquot and dilute each RNA oligo to a concentration of 50 µM.

Combine 30 µl of each RNA oligo solution and 15 µl of 5× annealing buffer. Final buffer concentration is: 100 mM potassium acetate, 30 mM HEPES-KOH pH 7.4, 2 mM magnesium acetate. Final volume is 75 µl.

Incubate the solution for 1 minute at 90° C., centrifuge the tube for 15 seconds, let sit for 1 hour at 37° C., then use at ambient temperature. The solution can be stored frozen at −20° C. and freeze-thawed up to 5 times. The final concentration of siRNA duplex is usually 20 µM.

Alternatively, already annealed dsRNAs may be purchased from the suppliers.

Chemically modified nucleic acids may also be used, For example, an overview of the types of modification which may be used is given in WO03/070744, the contents of which are incorporated herein by reference. Particular attention is drawn to pages 11 to 21 of this publication. Other possible modifications are as described above. The skilled person will be aware of other types of chemical modification which may be incorporated into RNA molecules.

"In vitro" System

TRPV1 expression has been detected in cutaneous sensory nerve fibers, mast cells, epidermal keratinocytes, dermal blood vessels, the inner root sheet and the infundibulum of hair follicles, differentiated sebocytes, sweat gland ducts, and the secretory portion of eccrine sweat glands by immunoreactivity assays (Stander et al., 2004). Upon reverse transcriptase-polymerase chain reaction and Western blot analysis, TRPV1 has been detected in mast cells and keratinocytes from human skin (Stander et al., 2004). Recently, dendritic cells have also shown to express TRPV1 (Basu & Srivastava, 2005) and neuronal cell models have been developed with cells that express TRPV1 (Lilja & Forsby, 2004).

Cell cultures expressing the target gene TRPV1 are used for a preliminary testing of the specificity of siRNA interference.

The cells are incubated with the corresponding siRNA duplexes, and analysis of the downregulation of expression of the target gene is carried out. For linking siRNA knockdown to specific phenotypes in cultured cells, it is necessary to demonstrate the decrease of the targeted protein or at least demonstrate the reduction of the targeted mRNA.

mRNA levels of the target gene can be quantitated by Real-time quantitative PCR (qRT-PCR). Further, the protein levels can be determined in a variety of ways well known in the art, such as Western blot analysis with specific antibodies to the target, which allow direct monitoring of the reduction of targeted protein.

Transfection of siRNA Duplexes in Cell Cultures

Several examples of techniques well known in the art are as follows: We can perform a single transfection of siRNA duplex using a cationic lipid, such as RNAiFect Transfection Reagent (Qiagen) and Lipofectamine 2000 Reagent (Invitrogen) and assay for silencing 24, 48 and 72 hours after transfection.

A typical transfection protocol can be performed as follows: For one well of a 6-well plate, we transfect using 100 nM as final concentration of siRNA. Following RNAiFect protocol, we seed, the day before transfection, 2-4×10$^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 15 ul of 20 uM siRNA duplex (corresponding to 100 nM final concentration) in 85 ul of Buffer EC-R, to give a final volume of 100 ul, and mix by vortexing. For complex formation, we add 19 ul of RNAiFect Transfection Reagent to the diluted siRNA and mix by pipetting or vortexing. After incubating the samples for 10-15 minutes at room temperature to allow formation of transfection complexes, we add the complexes drop-wise onto the cells with 2.9 ml of fresh growth medium low in antibiotics. After swirling the plates to ensure uniform distribution of the transfection complexes, we incubate the cells under their normal growth conditions. The day after, the complexes are removed and fresh and complete growth medium is added. To monitor gene silencing, cells are collected at 24, 48 and 72 hours post-transfection. The Lipofectamine 2000 Reagent protocol is quite similar. The day before transfection, we seed 2-4×10$^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 12.5 ul of 20 uM siRNA duplex (corresponding to 100 nM final concentration) in 250 ul of DMEM, to give a final volume of 262.5 ul, and mix. Also, 6 ul of Lipofectamine 2000 is diluted in 250 ul of DMEM and mixed. After a 5 minutes incubation at room temperature, the diluted oligomer and the diluted Lipofectamine are combined to allow complex formation during a 20 minutes incubation at room temperature. Afterwards, we add the complexes drop-wise onto the cells with 2 ml of fresh growth medium low in antibiotics and mix gently by rocking the plate back and forth, to ensure uniform distribution of the transfection complexes. We incubate the cells under their normal growth conditions and the day after, the complexes are removed and fresh and complete growth medium is added. To monitor gene silencing, cells are collected at 24, 48 and 72 hours post-transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/or fluorescence microscopy the next day.

Testing of siRNA Duplexes

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

After transfections, total RNA fractions extracted from cells are pre-treated with DNase I and used for reverse transcription using a random primer. PCR-amplification is carried out with a specific primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable protein may exist in the cell. Alternatively, Real-time PCR amplification can be used to test in a more precise way the mRNA decrease or disappearance. Real-time reverse-transcriptase (RT) PCR quantitates the initial amount of the template most specifically, sensitively and reproducibly. Real-time PCR monitors the fluorescence emitted during the reaction as an indicator of amplicon production during each PCR cycle, in a light cycler apparatus. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template.

To verify the interference pattern of TRPV1 gene in the cell cultures, qRT-PCR is performed according to the manufacturer protocol. For quantitative qRT-PCR, approximately 250-500 ng of total RNA are used for reverse transcription followed by PCR amplification with specific primers for TRPV1 in reaction mixture containing Master SYBR Green I. Basic PCR conditions comprise an initial step of 30 min at 91° C., followed by 40 cycles of 5 s at 95° C., 10 s at 62° C. and 15 s at 72° C. Quantification of b-actin mRNA can be used as a control for data normalization. Relative gene expression comparisons work best when the gene expression of the chosen endogenous/internal control is more abundant and remains constant, in proportion to total RNA, among the samples. By using an invariant endogenous control as an active reference, quantitation of an mRNA target can be normalised for differences in the amount of total RNA added to each reaction. The amplification curves obtained with the light cycler are analyzed in combination with the control kit RNA, which targets in vitro transcribed cytokine RNA template, according to the manufacturer protocol. In order to assess the specificity of the amplified PCR product a melting curve analysis is performed. The resulting melting curves allow discrimination between primer-dimers and specific PCR product.

Animal Studies

In vivo silencing effect of siNA molecules on TRPV1 expression levels can be tested on a guinea-pig cornea model such as the one described by Brock et al. Tetrodotoxin-resistant impulses in single nociceptor nerve terminals in guinea-pig cornea. J Physiol. 1998 Oct. 1; 512 (Pt 1):211-7.

The basic procedure consists on the instillation of the siNA molecule to be tested, contained in a small volume, on the guinea-pig corneal surface. Contralateral eyes are treated with the vehicle alone, and can be used as controls in each experiment lest there is a sympathy phenomenon with the other eye. Multiple experiments in the same animal should be abolished.

Extracellular recording of electrical activity of sensory axons of siNA-treated or control guinea pig cornea can be carried out as described in Brock et al. in 1998. Basically, eyes from guinea-pigs (150-300 g, killed with 100 mg kg-1 pentobarbitone I.P.) are mounted in a recording chamber and superfused with physiological saline of the following composition (mM): $Na^+$, 151; $K^+$, 4.7; $Ca^{2+}$, 2; $Mg^{2+}$, 1.2; $Cl^-$, 144; $H_2PO^-$, 1.3; $HCO_3^-$, 16.3; and glucose, 9.8. This solution is gassed with 95% $O_2$-5% $CO_2$ (to pH 7.4) and maintained at 31-33° C. The optic nerve and associated ciliary nerves are drawn into a suction stimulating electrode. The stimulus parameters are modified as required throughout the experiment (pulse width, 0.1-0.5 ms, 5-30 V). A glass recording electrode (tip outer diameter, 50 µm) filled with physiological saline is applied to the surface of the corneal epithelium with slight suction. Electrical activity is recorded through an AC amplifier (Neurolog NL104, Digitimer Ltd, Welwyn Garden City, UK; gain, 2000; high pass filter set at 0.1 Hz) and the output digitized at 44 kHz and stored on magnetic tape using a PCM recorder (A. R. Vetter Co. Inc., Rebersburg, Pa., USA). Recordings are only made from sites where the nerve impulses are readily distinguished from the noise (10 µV peak-to-peak when low pass filtered at 3-5 kHz). At many sites on the cornea, no evoked or spontaneous electrical activity is recorded or the signals are too small to be analysed. Internal perfusion of the recording electrode is achieved by inserting a fine plastic tube to within 200 µm of the electrode tip (see Brock & Cunnane, 1995, Effects of $Ca^{2+}$ and $K^+$ channel blockers on nerve impulses recorded from postganglionic sympathetic nerve terminals. The Journal of Physiology 489, 389-402). A MacLab data acquisition system (ADInstruments Pty Ltd, Castle Hill, NSW, Australia) is used to digitize (sampling frequencies, 10-20 kHz) electrophysiological signals previously recorded on tape. Prior to digitizing, the signals are filtered using a low pass filter (cutoff, 3-5 kHz). Subsequent analysis is made with the computer program Igor Pro (Wavemetrics, Lake Oswego, Oreg., USA). TRPV1 mRNA levels can be quantitated by Real-time quantitative PCR (qRT-PCR) while reduction in the protein levels can be directly monitored in a variety of ways well known in the art, such as Western blot analysis with specific antibodies to the target.

Downregulation of expression of TRPV1 by siNA in hair follicle can be monitored by means of the following representative models without excluding other animal models well known in the art:

In Vivo Mouse Hair Follicle Transfection. Under general anesthesia, dorsal skin of 50-day-old Balb/c mice (Charles River, Wilmington, Mass.) is clipped of hair and treated with a depilatory cream or a shaving machine (Neet; Premier Consumer Products, Inc., Englewood, N.J.) for 5 min. At different time points after depilation, 50 ml of lipoplex containing 50 mg of lipid and different amounts of individual siRNAs together with 10 mg of pCMV-b-gal is applied topically to 1 cm2 of dorsal skin in 5 ml aliquots using a micropipette over 90 min. DNA amounts are similar to previously published studies. Control skin is treated with a scrambled siRNA together with 10 mg naked plasmid or 50 mg of lipid alone. Transfected skin is harvested 24 or 48 h after transfection, and stained for b-gal activity.

Xenograft Model. Four-week-old CB-17 lcr-scid/scid male mice (Charles River, Wilmington, Mass.) are maintained under pathogen-free conditions. Human fetal scalp (20-week gestation from Advanced Bioscience Resources, Alameda, Calif.), or human adult scalp from cosmetic surgery is grafted within 24 h of harvest. Grafting surgery is performed in a laminarflow hood using sterile procedures. Mice are anesthetized with ketamine-xylazine mixture, after which hair on the dorsum is clipped. Pieces of skin measuring 1×1 cm are grafted to a bed of similar size that had been prepared by removing mouse skin down to the fascia. Human skin grafts (usually two per mouse) are held in place with 6-0 nonabsorbable monofilament suture. The transplants are coated with petrolatum and covered with Tegaderm (3M Health Care Ltd. (St. Paul, Minn.)), and sterile dressing. Bandages are removed after two to three weeks, and grafts are allowed to heal for an additional two to three weeks before proceeding with the experiments.

Transfection of Human Xenografts in Vivo. Before transfection, xenografts are depilated. Some grafts are also treated with 0.05% retinoic acid cream (Retin-A, Johnson & Johnson, Raritan, N.J.) every other day for one week. On the day of transfection, mice are anesthetized and the xenografts are prehydrated with PBS for 15 min. After 75 mg of pFx-1 lipid and 30 mg of pCMV-b-gal with or without individual siRNAs are mixed in OPTI-MEM, the mixture is pipetted topically in 5 ml aliquots (75 ml total) to the grafted skin every other day for three days. Higher doses of DNA and liposomes are used in human versus mouse transfections because of the thicker stratum corneum, which could potentially absorb the lipoplex and prevent adequate delivery to the follicle. Skin is harvested 48 h after transfection and processed for b-gal activity.

Histochemical Assays. Mouse and human tissue samples are fixed in freshly prepared 2% formaldehyde/0.2% glutaraldehyde in PBS at 4° C. for 2-4 h, then washed in three changes of PBS at room temperature for 1 h. Fixed tissue is incubated at 37° C. overnight in 1 mg ml-1 X-gal in PBS. Then tissue is washed with PBS, fixed in formalin, and embedded in paraffin. Sections of 5 mm are counterstained with nuclear fast red. Fixed biopsies can also be stained with specific antibodies to test the inhibition of expression of TRPV1. Staining is performed as reported previously. Some biopsy slices are kept on RNA later (Ambion) and processed for RNA purification. Total RNA is analysed using specific probes/primers for specific interference after individual siRNA treatments.

EXAMPLES

Example 1

In order to determine whether the behavioral response to topical application of the TRPV1 agonist capsaicin was modified by pretreatment with siRNA prepared against the guinea pig TRPV1, experiments were carried out in adult, male guinea pigs.

1-Effect of Topical Capsaicin.

Two guinea pigs were treated with 10 µL drop of a 0.1 mM capsaicin solution in the right eye and 10 µL of sterile isotonic saline in the left eye.

In the following 5 min following topical application the following parameters were measured:
  Blinking frequency
  Time of lid closure
  Scratching movements (with hind limb) and wiping movements (with the foreleg) directed to the treated eye.

After this 5 min period the following parameters were assessed:
  Conjunctival hyperemia and palpebral edema
  Tearing (with a Schirmer strip maintained 3 min in the subconjunctival sac).

Experiments were performed at 9:00 am during 4 consecutive days. Both eyes were treated simultaneously with the corresponding solution, and parameters were measured simultaneously by an independent observer for each eye.

All the measured parameters were higher in the capsaicin-treated eye when compared with the control (saline-treated). The parameters that were most consistently altered were the number of scratching/wiping movements, hyperemia and lacrimation.

FIG. 3 summarizes the results obtained in 2 animals. It is evident that capsaicin evoked scratching/wiping movements, conjunctival hyperemia and lacrimation that were absent in the saline-treated side. Also, no desensitization to repeated applications during successive days was observed.

2-Effect of oligonucleotide 3 (ON3), corresponding to SEQ ID NO 146 with dTdT overhangs in both 3' ends, on the capsaicin response.

The attenuating effect of ON3 on the behavioural response to topical capsaicin was initially explored in a group of 4 guinea pigs. Two doses of 15 µL of a solution containing the ON3 was applied topically to the right eye (treated eye) at 9:00 am during the days 0, 1 and 2. At 3:00 pm during days 1, 2, 3, 4, 7, 8 and 9, 10µ of 0.1 mM capsaicin solution were applied to both eyes and the behavioral response to the drug measured in each eye, according to the methods described above.

Figure 4:
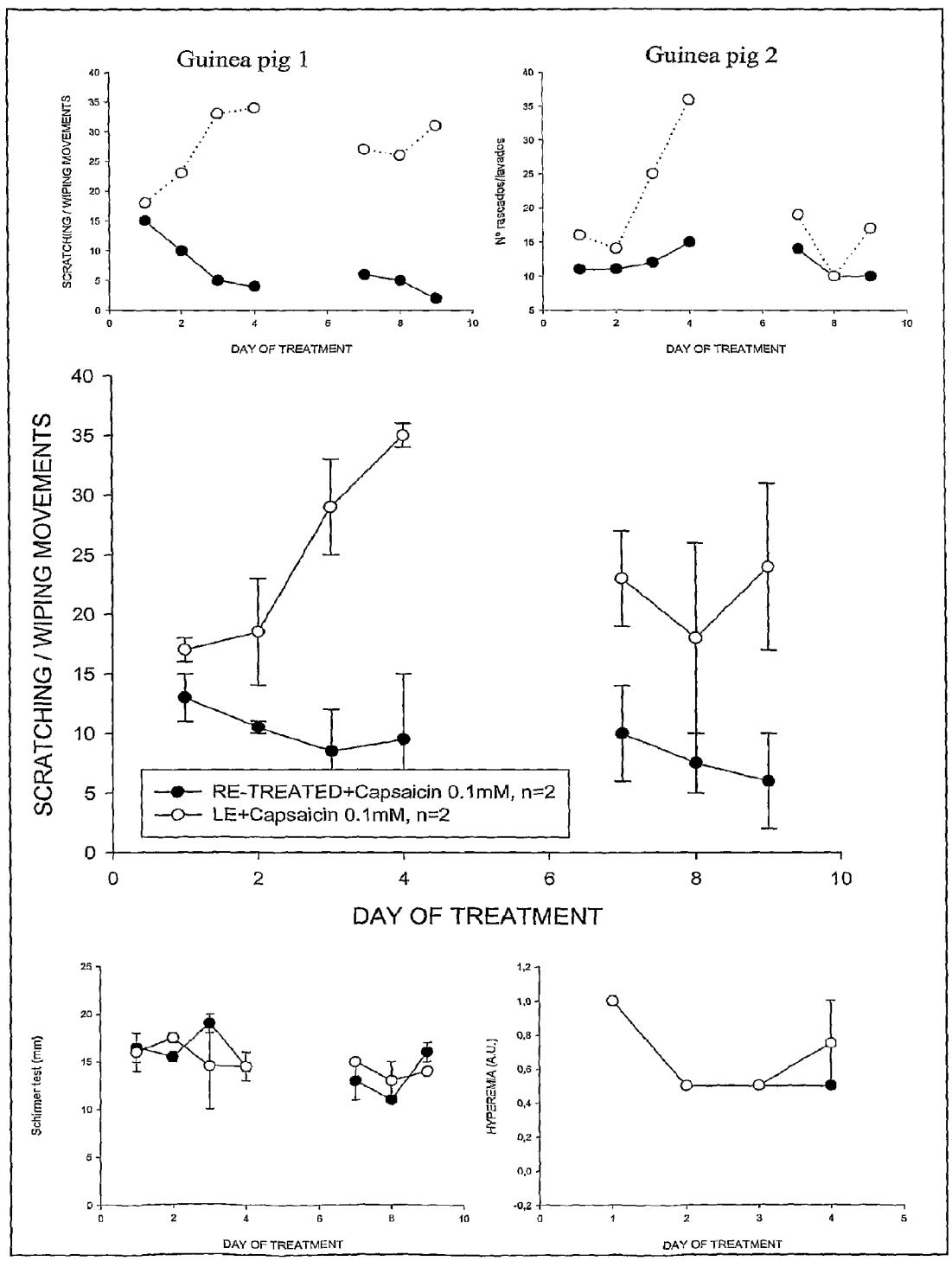
FIG. 4. Attenuating effect of ON3 on the behavioural response to topical capsaicin 0.1 mM. Scratching and wiping movements (A), Tearing (B) and Conjunctival hyperemia (C) were analysed.

As shown in FIG. 4, ON3 evoked a reduction of the behavioral response (number of scratching/wiping movements) to capsaicin application in comparison with untreated animals. This reduction was established gradually, starting on day 2 and augmenting in successive days. Seven days after treatment, differences in the response between ON3-treated and untreated eyes were still present. In contrast, tear secretion was not different between both eyes.

Figure 5:
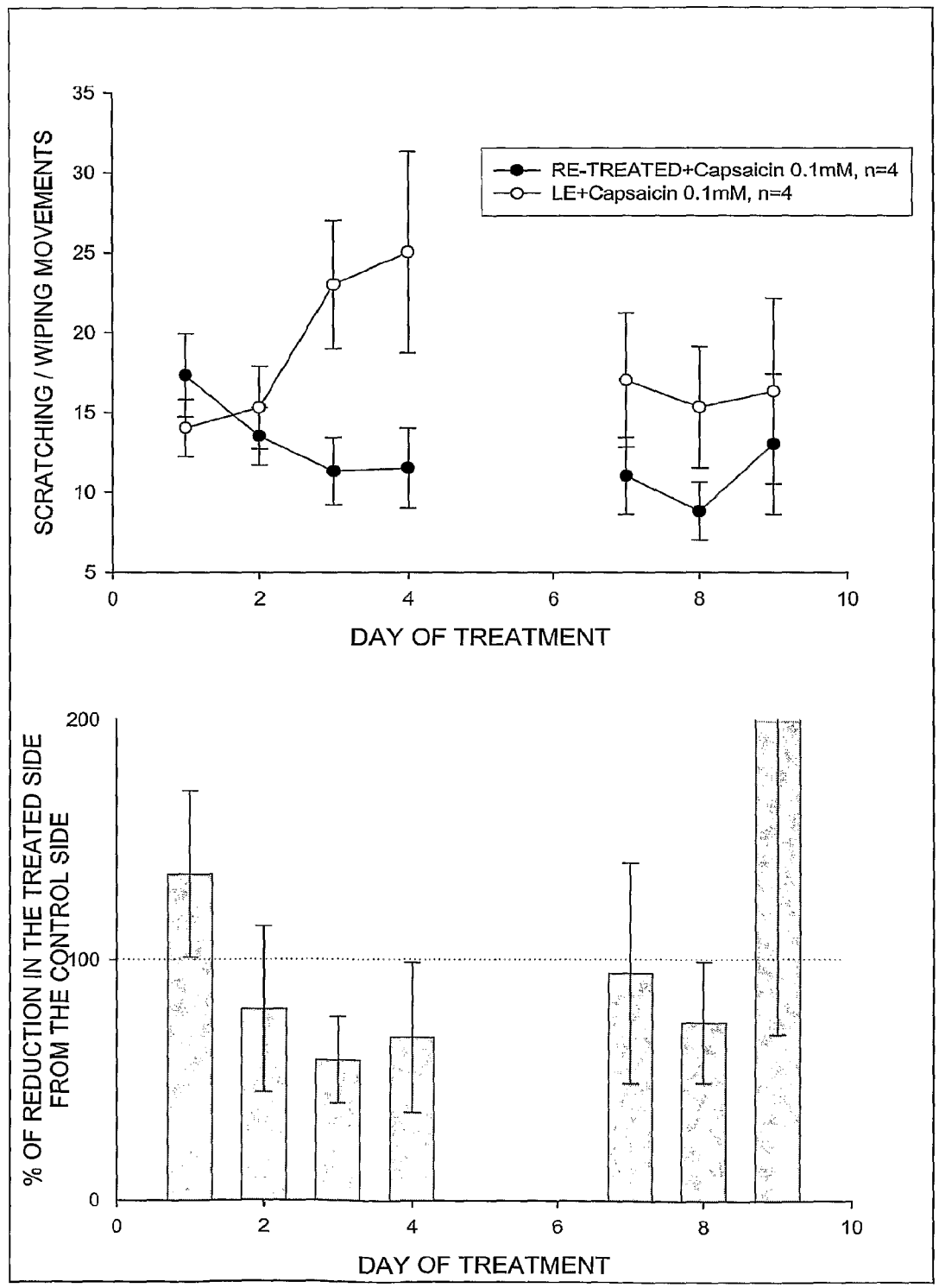
FIG. 5. Average reduction in the number of scratching/wiping movements in all the studied animals, presented in absolute values (upper graph) and as percentage of reduction in the treated side from the control side, at the various days after treatment.

FIG. 5 summarizes the average reduction in the number of scratching/wiping movements in all the studied animals, presented in absolute values (upper graph) and as percentage of reduction in the treated side from the control side, at the various days after treatment.

Example 2

Figure 6:
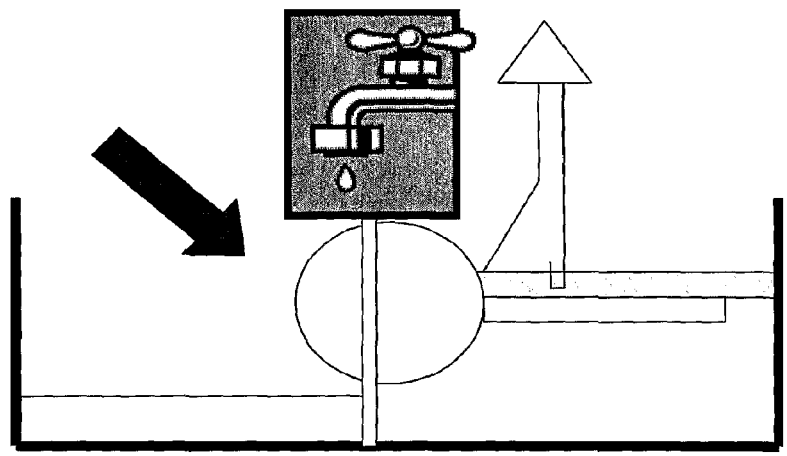
FIG. 6. Recording chamber configuration.

Eyes from deeply anesthetized guinea pigs were dissected free from their orbits and mounted in a divided recording chamber. The eye was continuously perfused with physiological solution of the following composition (mM): Na+, 151; K+, 4.7; Ca2+, 2; Mg2+, 1.2; Cl−, 144.5; H2PO3−, 1.3; HCO3−, 16.3; glucose, 7.8. This solution was gassed with carbogen (95% O2, 25% CO2) to pH 7.4 and maintained at approx 34° C. with a Peltier device. Activity of single corneal nerve fibers was recorded from the ciliary nerves at the back of the eye. The recording configuration is shown schematically in FIG. 6.

Control Eyes: Neural activity was recorded from 20 polymodal fibers obtained form 10 guinea pig eyes identified by their response to mechanical stimulation and by their response to a jet of gas containing CO2 (98%). In each fiber a sequence of stimuli was applied: a drop of capsaicin 0.1 mM followed by washing 30 sec later. Hot saline at 45° C. during 1 min, Pulse of CO2 applied during 30 s. Between each stimulus, a pause of 5 min was allowed. Three of these sequences were applied per single fiber with a 15 min interval between stimulation cycles. Quantification of the response was performed measuring the total number of impulses evoked by each stimulus during the stimulation period.

Treated Eyes: In 5 guinea pigs, both eyes were treated with 15 µL of a solution containing ON3 at 9:00 am every day during three consecutive days. On the fourth day, both eyes were enucleated and studied 'in vitro' as described above.

Nine fibers identified as polymodal nociceptor fibers were identified in these eyes. The same stimulation protocol used for control eyes, namely capsaicin, heat and CO2 stimuli applied sequentially with a 5 min pause between stimuli, repeated three times per fibers. Quantification of the response to each of these stimuli showed that the number of impulses evoked was significantly lower in ON3 treated animals. Reduction of the response in comparison with control eyes was: 60% for capsaicin, 56% for heat and 40% for acidic stimulation.

The invention claimed is:

1. A method of treating an eye disorder characterized by increased expression and/or activity of TRPV1, said method comprising topically administering to the corneal surface of the eye of a patient in need thereof a short interfering nucleic acid (siNA) directed against TRPV1 in an amount that reduces TRPV1 expression in the eye.

2. A method of treating an eye disorder characterized by increased expression and/or activity of TRPV1, said method comprising topically administering to the corneal surface of the eye of a patient in need thereof a short interfering nucleic acid (siNA) directed against TRPV1 in an amount that reduces ocular discomfort in the eye.

3. The method of claim 1 wherein the eye condition is selected from the group consisting of discomfort and altered sensitivity of the cornea following refractive surgery, use of contact lenses, dry eye, and diabetic retinopathy.

4. The method of claim 1 wherein the siNA is siRNA.

5. The method of claim 4 wherein the siRNA is dsRNA or shRNA.

6. The method of claim 1 wherein the siNA comprises a chemically modified oligonucleotide.

7. The method of claim 1 wherein a plurality of species of siNA are administered.

8. The method of claim 7 wherein each of said plurality of species is targeted to the same mRNA species.

9. The method of claim 1 wherein the siNA is targeted to a nucleotide sequence selected from the group consisting of SEQ ID NO: 1 to SEQ ID NO: 81 or to a nucleotide sequence comprising a nucleotide sequence selected from the group consisting of SEQ ID NO: 1 to SEQ ID NO: 81.

10. The method of claim 1 wherein the siNA consists of a nucleotide sequence of 40 nucleotides or less comprising a nucleotide sequence selected from the group consisting of SEQ ID NO: 82 to SEQ ID NO: 162.

11. The method of claim 10 wherein the siNA is hybridized to its complement to make a dsRNA.

12. The method of claim 11 wherein the dsRNA has a 3' overhang.

13. The method of claim 12 wherein the 3' overhang is a dinucleotide overhang of thymidine nucleotides.

14. A siNA compound targeted to TRPV1 comprising a nucleotide sequence complementary to the nucleotide sequence of SEQ ID NO: 65.

15. The siNA compound of claim 14 comprising the nucleotide sequence of SEQ ID NO: 146.

16. The siNA compound of claim 15 comprising the nucleotide sequence of SEQ ID NO: 146 with thymidine dinucleotide overhangs at both 3' ends of said nucleotide sequence.

17. A pharmaceutical composition comprising the compound of claim 14.

* * * * *